(12) United States Patent
Ameri

(10) Patent No.: US 8,170,680 B2
(45) Date of Patent: May 1, 2012

(54) IMPLANTABLE MULTI-LENGTH RF ANTENNA

(75) Inventor: Masoud Ameri, Maple Plain, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 353 days.

(21) Appl. No.: 12/397,199

(22) Filed: Mar. 3, 2009

(65) Prior Publication Data

US 2009/0228076 A1   Sep. 10, 2009

Related U.S. Application Data

(60) Provisional application No. 61/033,535, filed on Mar. 4, 2008, provisional application No. 61/087,476, filed on Aug. 8, 2008.

(51) Int. Cl.
*A61N 1/36* (2006.01)
(52) U.S. Cl. .......................................... 607/60; 607/30
(58) Field of Classification Search .................. 607/60, 607/30
See application file for complete search history.

(56) References Cited

U.S. PATENT DOCUMENTS

| | | | |
|---|---|---|---|
| 3,944,722 A | 3/1976 | Larsen | |
| 4,134,120 A | 1/1979 | DeLoach et al. | |
| 5,246,438 A | 9/1993 | Langberg | |
| 5,258,765 A | 11/1993 | Dörrie et al. | |
| 5,861,019 A | 1/1999 | Sun et al. | |
| 6,009,350 A | 12/1999 | Renken | |
| 6,167,312 A | 12/2000 | Goedeke | |
| 6,169,925 B1 | 1/2001 | Villaseca et al. | |
| 6,205,358 B1 | 3/2001 | Haeg et al. | |
| 6,456,256 B1 | 9/2002 | Amundson et al. | |
| 6,505,072 B1 | 1/2003 | Linder et al. | |
| 6,574,510 B2 | 6/2003 | Von Arx et al. | |
| 6,614,406 B2 | 9/2003 | Amundson et al. | |
| 6,708,065 B2 | 3/2004 | Von Arx et al. | |
| 6,804,561 B2 | 10/2004 | Stover | |
| 6,809,701 B2 | 10/2004 | Amundson et al. | |
| 6,868,288 B2 | 3/2005 | Thompson | |
| 7,016,733 B2 | 3/2006 | Dublin et al. | |
| 7,047,076 B1* | 5/2006 | Li et al. ........................ | 607/36 |

(Continued)

FOREIGN PATENT DOCUMENTS

EP    0505673 A1    9/1992

(Continued)

OTHER PUBLICATIONS

"U.S. Appl. No. 09/798,249, Notice of Allowance mailed Oct. 21, 2003", 5 pgs.

(Continued)

*Primary Examiner* — Carl H Layno
*Assistant Examiner* — Paula J Stice
(74) *Attorney, Agent, or Firm* — Schwegman, Lundberg & Woessner, P.A.

(57) ABSTRACT

A system and method for wirelessly transferring information electromagnetically at a specified first operating frequency range in a first medium and at a specified second operating frequency range in a second medium using an implantable multi-length antenna. The implantable multi-length antenna can be configured to appear electrically as a first electrical length in the first medium and as a different second electrical length in the second medium. In other examples, the first operating frequency range can be specified using the first electrical length and the second operating frequency range can be specified using the second electrical length.

20 Claims, 14 Drawing Sheets

U.S. PATENT DOCUMENTS

| | | |
|---|---|---|
| 7,072,718 B2 | 7/2006 | Von Arx et al. |
| 7,149,578 B2 | 12/2006 | Edvardsson |
| 7,289,855 B2 | 10/2007 | Nghiem et al. |
| 7,309,262 B2 | 12/2007 | Zart et al. |
| 7,313,441 B2 | 12/2007 | Mass et al. |
| 7,317,946 B2 | 1/2008 | Twetan et al. |
| 7,319,901 B2 | 1/2008 | Dublin et al. |
| 7,363,087 B2 | 4/2008 | Nghiem et al. |
| 7,483,752 B2 | 1/2009 | Von Arx et al. |
| 2001/0034543 A1 | 10/2001 | Haeg |
| 2002/0065539 A1 | 5/2002 | Von Arx et al. |
| 2002/0095195 A1 | 7/2002 | Mass et al. |
| 2002/0123776 A1 | 9/2002 | Von Arx et al. |
| 2003/0018246 A1 | 1/2003 | Govari et al. |
| 2003/0025645 A1 | 2/2003 | Amundson et al. |
| 2003/0114897 A1 | 6/2003 | Von Arx et al. |
| 2003/0117340 A1 | 6/2003 | Sheng-Gen et al. |
| 2003/0195589 A1 | 10/2003 | Von Arx et al. |
| 2004/0027306 A1 | 2/2004 | Amundson et al. |
| 2004/0095289 A1 | 5/2004 | Bae et al. |
| 2004/0176811 A1 | 9/2004 | Von Arx et al. |
| 2005/0113886 A1 | 5/2005 | Fischell et al. |
| 2005/0134520 A1* | 6/2005 | Rawat et al. .................. 343/873 |
| 2005/0203583 A1 | 9/2005 | Twetan et al. |
| 2005/0203584 A1 | 9/2005 | Twetan et al. |
| 2005/0222633 A1 | 10/2005 | Edvardsson |
| 2006/0089682 A1 | 4/2006 | Kronich et al. |
| 2006/0224206 A1 | 10/2006 | Dublin |
| 2006/0247711 A1 | 11/2006 | Verhoef et al. |
| 2006/0247712 A1 | 11/2006 | Fuller et al. |
| 2006/0287693 A1 | 12/2006 | Kraft et al. |
| 2007/0119741 A1 | 5/2007 | Wenger et al. |
| 2007/0142829 A1 | 6/2007 | Ahn |
| 2007/0179554 A1 | 8/2007 | Iyer et al. |
| 2007/0222697 A1 | 9/2007 | Caimi et al. |
| 2007/0260294 A1 | 11/2007 | Schulman et al. |
| 2007/0288065 A1 | 12/2007 | Christman et al. |
| 2007/0288066 A1 | 12/2007 | Christman et al. |
| 2008/0021522 A1 | 1/2008 | Verhoef et al. |
| 2008/0039898 A1 | 2/2008 | Lim et al. |
| 2009/0192574 A1 | 7/2009 | Von Arx et al. |
| 2009/0228074 A1 | 9/2009 | Edgell |
| 2009/0228075 A1 | 9/2009 | Dion |

FOREIGN PATENT DOCUMENTS

| | | |
|---|---|---|
| EP | 1537895 A1 | 6/2005 |
| EP | 1362614 B1 | 3/2008 |
| JP | 2001068917 | 3/2001 |
| JP | 2004080713 | 3/2004 |
| WO | WO-98/48895 A1 | 11/1998 |
| WO | WO-0016439 | 3/2000 |
| WO | WO-02/31909 A1 | 4/2002 |
| WO | WO-03/053515 A1 | 7/2003 |
| WO | WO-2005/123186 | 12/2005 |
| WO | WO-2006/060750 A1 | 6/2006 |
| WO | WO-2006104847 A1 | 10/2006 |
| WO | WO-2006/131302 A1 | 12/2006 |
| WO | WO-2009/111009 A1 | 9/2009 |
| WO | WO-2009/111012 A1 | 9/2009 |

OTHER PUBLICATIONS

"U.S. Appl. No. 09/798,249, Non-Final Office Action mailed Mar. 28, 2003", 7 pgs.

"U.S. Appl. No. 09/798,249, Response filed Jul. 28, 2003 to Non Final Office Action mailed Mar. 28, 2003", 8 pgs.

"U.S. Appl. No. 10/800,596, Response filed Feb. 4, 2008 to Final Office Action mailed Dec. 4, 2007", 6 pgs.

"U.S. Appl. No. 10/800,596, Amendment and Response filed Jun. 7, 2007 to Final Office Action mailed Mar. 7, 2007", 8 pgs.

"U.S. Appl. No. 10/800,596, Final Office Action mailed Mar. 7, 2007", 7 pgs.

"U.S. Appl. No. 10/800,596, Non-Final Office Action mailed Jun. 28, 2007", 6 pgs.

"U.S. Appl. No. 10/800,596, Response filed Jun. 3, 2008 to Non-Final Office Action mailed Mar. 3, 2008", 8 pgs.

"U.S. Appl. No. 10/800,596, Response filed Sep. 28, 2007 to Non-Final Office Action mailed Jun. 28, 2007", 8 pgs.

"U.S. Appl. No. 10/800,596, Final Office Action mailed Dec. 4, 2007", 4 pgs.

"U.S. Appl. No. 10/800,596, Non-Final Office Action mailed Mar. 3, 2008", 9 pgs.

"International Application Serial No. PCT/US2009/001354, International Search Report mailed May 20, 2009", 5 pgs.

"International Application Serial No. PCT/US2009/001354, Written Opinion mailed May 20, 2009", 7 pgs.

"International Application Serial No. PCT/US2009/001349, International Search Report mailed May 20, 2009", 5 pgs.

"International Application Serial No. PCT/US2009/001349, Written Opinion mailed May 20, 2009", 7 pgs.

Basset, P., et al., ""Chip-Size" Antennas for Implantable Sensors and Smart Dust", *The 13th International Conference on Solid-State Sensors, Actuators and Microsystems. Digest of Technical Papers. Transducers '05*, (Seoul, Korea, Jun. 5-9, 2005), (2005), 457-460.

Gosalia, K., et al., "Investigation of a Microwave Data Telemetry Link for a Retinal Prosthesis", *IEEE Transactions on Microwave Theory and Techniques*, 52(8), (2004), 1925-1933.

Gosalia, K., "Novel Compact Antennas for Biomedical Implants Applications", *Dissertation, PhD, Electrical Engineering*, Graduate Faculty of North Carolina State University, (2004), 172 pgs.

Jacobsen, S., et al., "Characteristics of Microstrip Muscle-Loaded Single-Arm Archimedean Spiral Antennas as Investigated by FDTD Numerical Computations", *IEEE Transactions on Biomedical Engineering*, 52(2), (2005), 321-330.

Johansson, A. J., "Performance Measures of Implant Antennas", *First European Conference on Antennas and Propagation (EuCAP 2006)*, (Nice, France, Nov. 6-10, 2006), (2006), 1-4.

Karacolak, T., et al., "Design of a Dual-Band Implantable Antenna and Development of Skin Mimicking Gels for Continuous Glucose Monitoring", *IEEE Transcations on Microwave Theory and Techniques*, 56(4), (Apr. 2008), 1001-1008.

Kim, J., et al., "An Implanted Antenna in the Spherical Human Head: SAR and Communication Link Performance", *IEEE Topical Conference on Wireless Communication Technology*, (2003), 202-203.

Kim, J., et al., "Implanted Antennas Inside a Human Body: Simulations, Designs, and Characterizations", *IEEE Transactions on Microwave Theory and Techniques*, 52(8), (2004), 1934-1943.

Ma, L., et al., "A Wearable Flexible Multi-Band Antenna Based on a Square Slotted Printed Monopole", *2008 Loughborough Antennas & Propagation Conference (LAPC 2008)*, (Mar. 17-18, 2008, Loughborough, United Kingdom), (2008), 345-348.

Neirynck, D., et al., "Exploiting Multiple-Input Multiple-Output in the Personal Sphere", *IEt Microwaves, Antennas & Propagation*, 1(6), (2007), 1170-1176.

"U.S. Appl. No. 12/397,180, Notice of Allowance mailed Jun. 14, 2011", 9 pgs.

"U.S. Appl. No. 12/397,187, Non-Final Office Action mailed Oct. 3, 2011", 10 pgs.

"Japanese Application Serial No. 2010-548748, Office Action mailed Oct. 4, 2011", (w/ English Translation), 5 pgs.

"Japanese Application Serial No. 2010-549652, Office Action mailed Oct. 4, 2011", (w/ English Translation), 6 pgs.

* cited by examiner

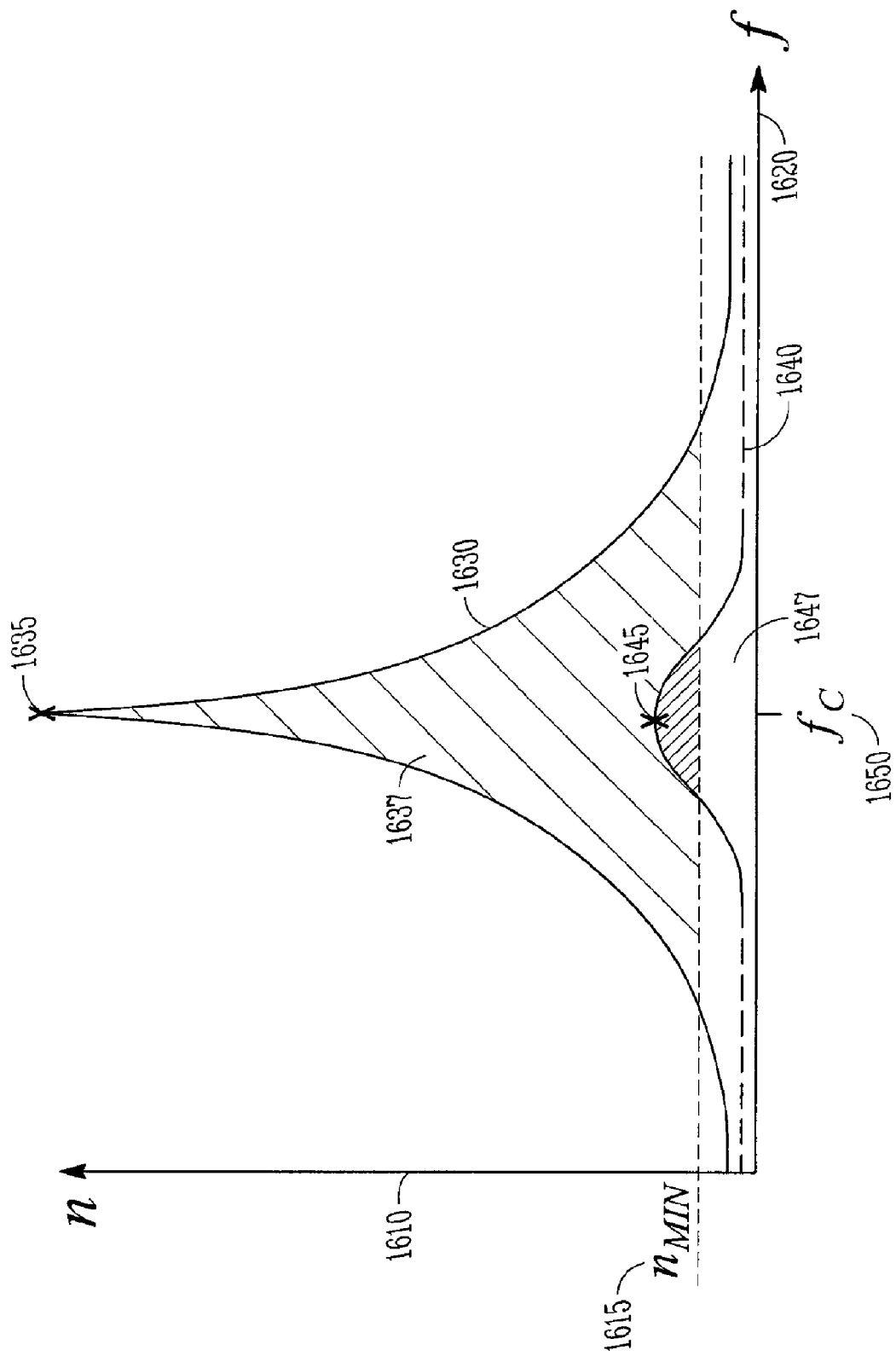

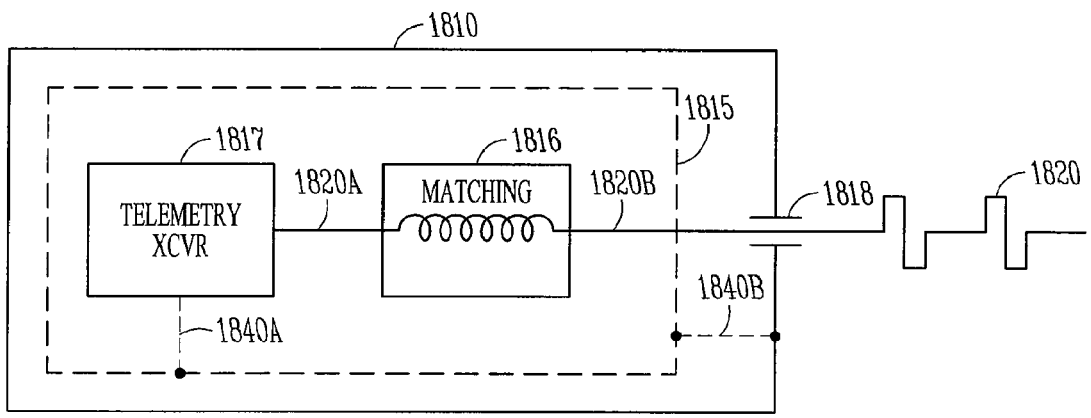
*FIG. 18*
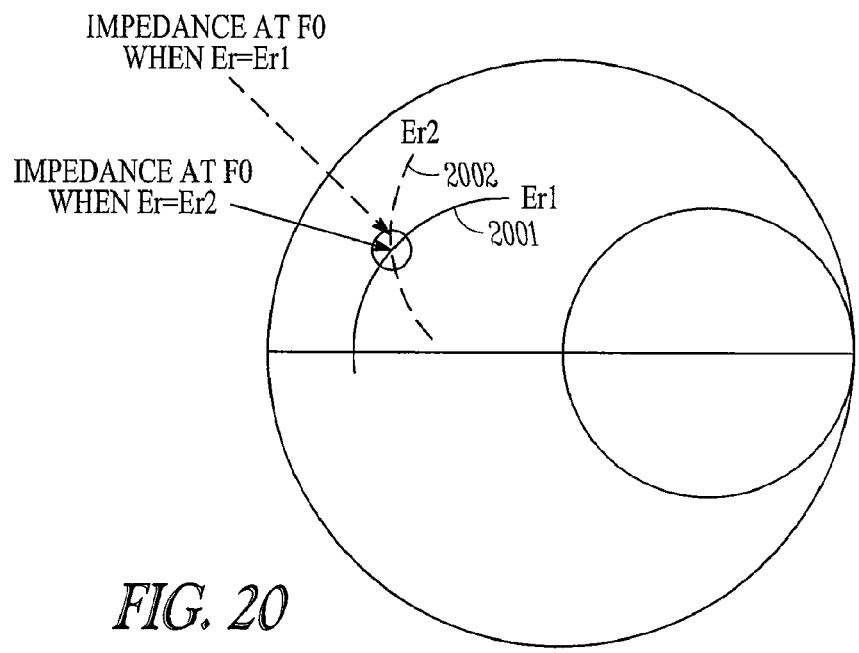
*FIG. 19*
*FIG. 20*

IMPLANTABLE MULTI-LENGTH RF ANTENNA

CROSS REFERENCE TO RELATED APPLICATIONS

This patent application claims the benefit of priority, under 35 U.S.C. Section 119(e), to Greg Carpenter et al., U.S. Provisional Patent Application Ser. No. 61/033,535, entitled "ANTENNA FOR IMPLANTABLE MEDICAL DEVICE," filed on Mar. 4, 2008, incorporated herein by reference in its entirety.

This patent application also claims the benefit of priority, under 35 U.S.C. Section 119(e), to Masoud Ameri, U.S. Provisional Patent Application Ser. No. 61/087,476, entitled "IMPLANTABLE MULTI-LENGTH RF ANTENNA," filed on Aug. 8, 2008, incorporated herein by reference in its entirety.

BACKGROUND

Medical devices can be implanted in a body to perform tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. An examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system. In certain examples, the implantable medical device can include a telemetry circuit and an antenna, coupled to the telemetry circuit, the combination of which can be configured to provide wireless communication between the implantable medical device and an external device, e.g., to send information (such as physiological or other information) from the implantable medical device to the external device, or to receive information (e.g., such as programming instructions) at the implantable medical device from the external device.

Magnetic coupling can be used to provide short-range (e.g., a few centimeters) communication between an implantable medical device implanted in a body and an external device, or between an implantable medical device outside of the body and an external device. However, magnetic coupling communication largely relies on near-field radiation, where the field distribution is highly dependent upon the distance from, and orientation of, the antenna, which grossly limits the effective range of wireless communication between the implantable medical device and the external device.

As an alternative to magnetic coupling communication, or in addition to magnetic coupling communication, low power radio frequency (RF) communication can be used to provide communication between an implantable medical device and an external device having an extended range over magnetic coupling. However, current RF communication circuits and antennas tuned for radiation from within a body tend to provide poor radiation outside of the body, and vice versa.

OVERVIEW

This document discusses, among other things, a system and method for wirelessly transferring information electromagnetically at a specified first operating frequency range in a first medium and at a specified second operating frequency range in a second medium using an implantable multi-length antenna. In certain examples, the implantable multi-length antenna can be configured to appear electrically as a first electrical length in the first medium and as a different second electrical length in the second medium. In certain examples, the first operating frequency range can be specified using the first electrical length and the second operating frequency range can be specified using the second electrical length.

In Example 1, a system includes an implantable telemetry circuit and an implantable multi-length antenna, the implantable multi-length antenna electrically connected to the implantable telemetry circuit and configured to wirelessly transfer information electromagnetically at a specified first operating frequency range in a first medium and at a specified second operating frequency range in a different second medium, and wherein the implantable multi-length antenna is configured to appear electrically as a first electrical length in the first medium and as a different second electrical length in the second medium, and wherein the first operating frequency range is specified using the first electrical length and the second operating frequency range is specified using the second electrical length.

In Example 2, the first operating frequency range of Example 1 is optionally substantially equal to the second operating frequency range.

In Example 3, the first operating frequency range of any one or more of Examples 1-2 optionally includes at least one of
 (a) a medical implant communication service (MICS) range from approximately 402 MHz to 405 MHz;
 (b) a short range device (SRD) range from approximately 862 MHz to 870 MHz;
 (c) a first industrial scientific and medical (ISM) range from approximately 902 MHz to 928 MHz; or
 (d) a second ISM range from approximately 2400 MHz to 2500 MHz.

In Example 4, the first medium of any one or more of Examples 1-3 optionally includes a dielectric material having a relative dielectric constant of approximately 1, and wherein the second medium of any one or more of Examples 1-3 optionally includes a dielectric material having a relative dielectric constant greater than or equal to 5.0.

In Example 5, the first medium of any one or more of Examples 1-4 is optionally air, and the second medium of any one or more of Examples 1-4 is optionally a biological medium, wherein the biological medium includes at least one of bodily fluid, skin tissue, fat tissue, muscle tissue, organ tissue, or bone.

In Example 6, the first electrical length in the first medium of any one or more of Examples 1-5 is optionally different than the second electrical length in the second medium due at least in part to a difference in a relative dielectric constant of the first medium and a relative dielectric constant of the second medium.

In Example 7, the first electrical length in the first medium of any one or more of Examples 1-6 is optionally different than the second electrical length in the second medium due at least in part to a capacitive coupling of at least a portion of the multi-length antenna in at least one of the first medium or the second medium.

In Example 8, the implantable multi-length antenna of any one or more of Examples 1-7 optionally includes a first segment positioned approximately parallel to a first axis, a first switchback, electrically connected to the first segment, and a second segment electrically connected to the first switchback, the second segment approximately parallel to the first axis. In Example 8, the first switchback of any one or more of Examples 1-7 optionally comprises (1) a first switchback segment electrically connected to the first segment using a first transition segment, the first switchback segment approximately parallel to a second axis, (2) a second switchback segment electrically connected to the first switchback segment using a second transition segment, the second switchback segment approximately parallel to the second axis, and (3) a third transition segment.

In Example 9, in the second medium, the first switchback segment of any one or more of Examples 1-8 optionally capacitively couples to the second switchback segment, and the second electrical length in the second medium of any one or more of Examples 1-8 is optionally less than the first electrical length in the first medium due at least in part to the capacitive coupling of the first switchback segment and the second switchback segment in the second medium.

In Example 10, at least one of the first switchback segment or the second switchback segment of any one or more of Examples 1 optionally comprise an arc shaped segment having a constant radius from a specified position.

In Example 11, the second axis of any one or more of Examples 1-10 is optionally substantially perpendicular to the first axis, and the implantable multi-length antenna of any one or more of Examples 1-10 optionally includes a second switchback electrically connected to the second segment, wherein the first switchback is positioned in a plane defined by the first axis and the second axis, and wherein the second switchback is positioned in a plane defined by the first axis and a third axis, wherein the third axis is substantially perpendicular to the first axis and different than the second axis.

In Example 12, the implantable multi-length antenna of any one or more of Examples 1-11 optionally includes a second switchback electrically connected to the second segment, the second switchback located a first distance from the first switchback, a third segment electrically connected to the second switchback, the third segment approximately parallel to the first axis, and a third switchback electrically connected to the third segment, the third switchback located a second distance from the second switchback, wherein the first distance is different than the second distance.

In Example 13, the implantable multi-length antenna of any one or more of Examples 1-12 is optionally configured to wirelessly transfer information electromagnetically at a specified third operating frequency range in the first medium and at a specified fourth operating frequency range in the second medium, wherein the third operating frequency range is different than the first operating frequency range and the fourth operating frequency range is different than the second operating frequency range, wherein the first operating frequency range and the second operating frequency range are specified using the first distance between the first switchback, and wherein the third operating frequency range and the fourth operating frequency range are specified using the second distance between the second switchback and the third switchback.

In Example 14, a method includes wirelessly transferring information electromagnetically at a specified first operating frequency range in a first medium and a specified second operating frequency range in a different second medium using an implantable multi-length antenna, wherein the implantable multi-length antenna is configured to appear electrically as a first electrical length in the first medium and as a different second electrical length in the second medium, and wherein the first operating frequency range is specified using the first electrical length and the second operating frequency range is specified using the second electrical length.

In Example 15, the first operating frequency range of Example 14 is optionally substantially equal to the second operating frequency range.

In Example 16, the first operating frequency range of any one or more of Examples 14-15 optionally includes at least one of
(1) a medical implant communication service (MICS) range from approximately 402 MHz to 405 MHz;
(2) a short range device (SRD) range from approximately 862 MHz to 870 MHz;
(3) a first industrial scientific and medical (ISM) range from approximately 902 MHz to 928 MHz; or
(4) a second ISM range from approximately 2400 MHz to 2500 MHz.

In Example 17, the first medium of any one or more of Examples 14-16 optionally includes a dielectric material having a relative dielectric constant of approximately 1, and wherein the second medium of any one or more of Examples 14-16 optionally includes a dielectric material having a relative dielectric constant greater than or equal to 5.0.

In Example 18, the first medium of any one or more of Examples 14-17 is optionally air, and wherein the second medium is a biological medium, wherein the biological medium includes at least one of bodily fluid, skin tissue, fat tissue, muscle tissue, organ tissue, or bone.

In Example 19, the first electrical length in the first medium of any one or more of Examples 14-18 is optionally different than the second electrical length in the second medium due at least in part to a difference in a relative dielectric constant of the first medium and a relative dielectric constant of the second medium In Example 20, the first electrical length in the first medium of any one or more of Examples 14-19 is optionally different than the second electrical length in the second medium due at least in part to a capacitive coupling of at least a portion of the multi-length antenna in at least one of the first medium or the second medium.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 16 illustrates generally an example of a radiation efficiency of an implantable multi-length antenna substantially surrounded by two different media.

FIG. 18 illustrates generally an example of at least a portion of a system including a telemetry circuit coupled to an implantable multi-length antenna.

FIG. 19 illustrates generally an example of a process including wirelessly transferring information electromagnetically at a first operating frequency range in a first medium and wirelessly transferring information electromagnetically at a second operating frequency range in a second medium.

FIG. 20 illustrates generally a relationship between an effective impedance of an antenna and a relative permittivity of a medium.

DETAILED DESCRIPTION

Figure 1:
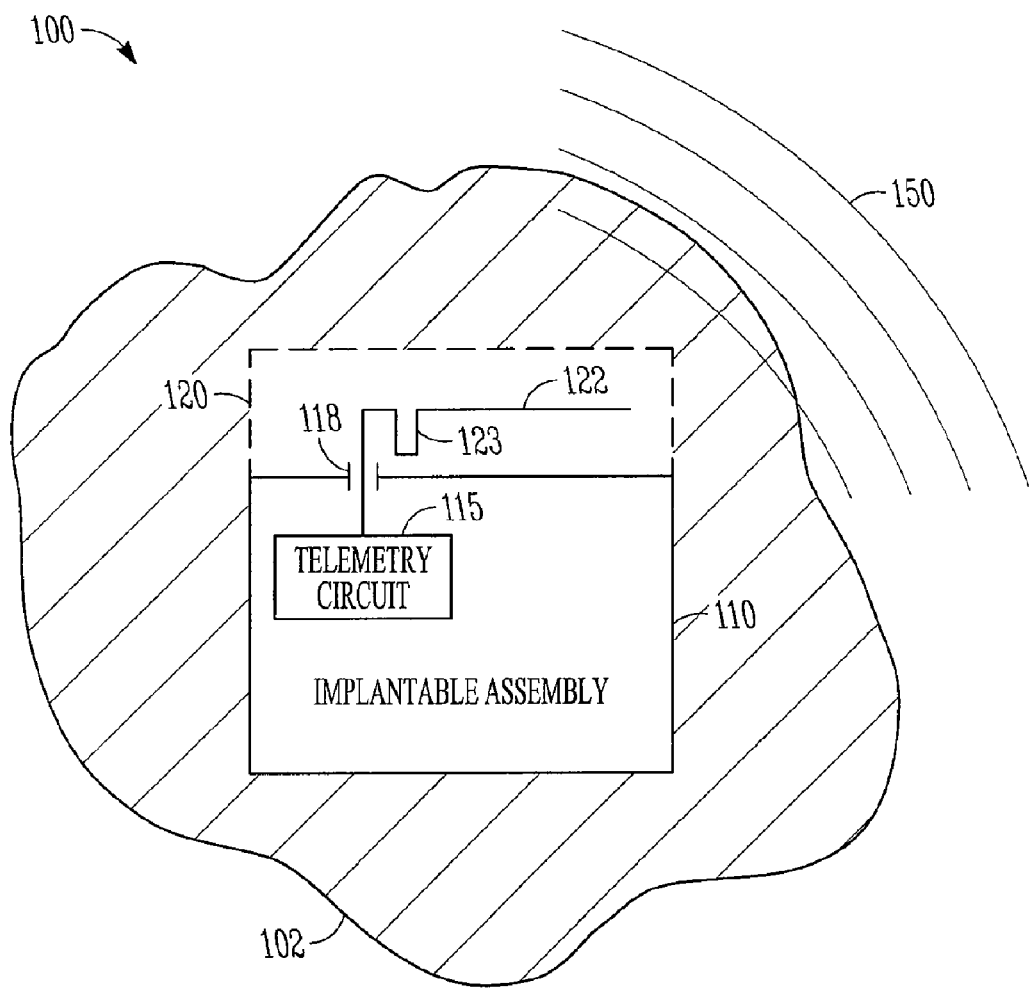
FIG. 1 illustrates generally an example of a system including an implantable telemetry circuit and an implantable antenna.

In certain examples, it can be desirable to establish a communication link between an implantable medical device and an external device before implanting the implantable medical device in a body, e.g., to test, program, or otherwise send information to or receive information from the implantable medical device, as well as after implanting the implantable medical device in the body, e.g., to program, monitor, or otherwise send information to or receive information from the implantable medical device. In an example, various wireless communication systems can provide communication between an external device and an implantable medical device both inside of and outside of the body. However, many communication systems tuned to radiate efficiently at a given frequency inside of the body do so poorly outside of the body. In other examples, a wireless communication system can include more than one telemetry circuit or antenna, the telemetry circuits or antennas individually tuned to radiate efficiently inside a human or animal body.

The present inventor has recognized, among other things, that it can be advantageous to use a single telemetry circuit, a single antenna, or a single combination of a telemetry circuit and an antenna to provide a communication link between the implantable medical device and the external device before implant as well as after implant, e.g., to reduce the number of system components, to reduce the overall size of the device, etc.

The present inventor has recognized, among other things, that one or more antenna characteristics can be used to tune or otherwise configured a single antenna to provide communication in more than one media (e.g., tissue, air, etc.) having one or more different transmission characteristics (e.g., different relative dielectric constants, etc.). In an example, utilizing a difference in relative dielectric constants in different media (e.g., between air and tissue), a single antenna can be configured have different electrical lengths in different media. In an example, in a first media having a first relative dielectric constant, a first portion of an antenna can exhibit little to no capacitive coupling to a second portion of the antenna or other conductor. However, in a second media having a second relative dielectric constant, the first portion of the antenna can exhibit a higher amount of capacitive coupling than in the first media to the second portion of the antenna or other conductor, thus effectively changing the electrical length of the antenna due to the higher capacitive coupling.

In an example, in free space, or in a medium having a relative dielectric constant of approximately 1, an antenna can be configured to have a desired length approximately equal to one quarter of a specified operating wavelength. In other examples, in free space, or in the medium having the relative dielectric constant of approximately 1, the antenna can be configured to have an acceptable length shorter than the desired length equal to one quarter of the specified operating wavelength. In certain examples, the shorter length can become necessary because otherwise, the quarter wavelength can become too long to work with. Generally, the desired length of the antenna changes roughly inversely proportionately to the square root of the relative dielectric constant of the medium surrounding the antenna. Thus, as the relative dielectric of the medium increases, the desired antenna length decreases.

The present inventor has recognized, among other things, that because a desired length of an antenna at a first specified operating frequency in free space is longer than a desired length of an antenna at the first specified operating frequency in tissue, and because the relative dielectric constant of tissue is different than the relative dielectric constant of free space, a coupling, such as a capacitive coupling, between one or more portions of an antenna can be utilized to provide a single antenna having a first electrical length equal to the desired length at a first specified operating frequency in free space and having a second electrical length equal to the desired length at the first specified operating frequency in tissue.

In an example, the antenna can include a first impedance corresponding to the first electrical length in the first medium, and a second impedance corresponding to the second electrical length in the second medium. In an example, the antenna can be tuned, designed, or configured in such a way that the first and second impedance are the same, so that a single matching network can optimize the radiation of the antenna.

FIG. 1 illustrates generally an example of a system 100 including an implantable telemetry circuit 115 and an implantable antenna 120. In an example, the system 100 can include an implantable assembly housing 110 configured to house at least a portion of an implantable telemetry circuit 115. In an example, the implantable assembly housing 110 can be made of a conductive biocompatible material, such as titanium. In certain examples, the implantable antenna 120 can be driven by the telemetry circuit 115 via a feed-through 118 through the implantable assembly housing 110. In an example, the feed-through 118 can prevent the implantable assembly housing 110 from attenuating, shorting out, or otherwise altering the radiation of electromagnetic energy 150 by the implantable antenna 120.

In an example, the implantable antenna 120 can include a switchback 122 and a non-switchback segment 123 configured to radiate electromagnetic energy 150 or to receive radiated electromagnetic energy 150 over one or more specified frequency ranges.

In an example, the implantable antenna 120 can be configured to radiate electromagnetic energy 150 or to receive radiated electromagnetic energy 150 when substantially surrounded by a first or a second medium. In an example, the first medium can include at least one of free space or air. In other examples, the second medium can include an implant medium 102. In certain examples, the implant medium 102 can include a biological medium, such as bodily fluid, skin tissue, fat tissue, muscle tissue, organ tissue, bone, or other biological medium. In an example, the implant medium 102 can include a portion of a human or a portion of an animal (e.g., an implantable medical device (IM) can be used as a monitoring device or therapy delivery device for pets, livestock, etc.)

Figure 2:
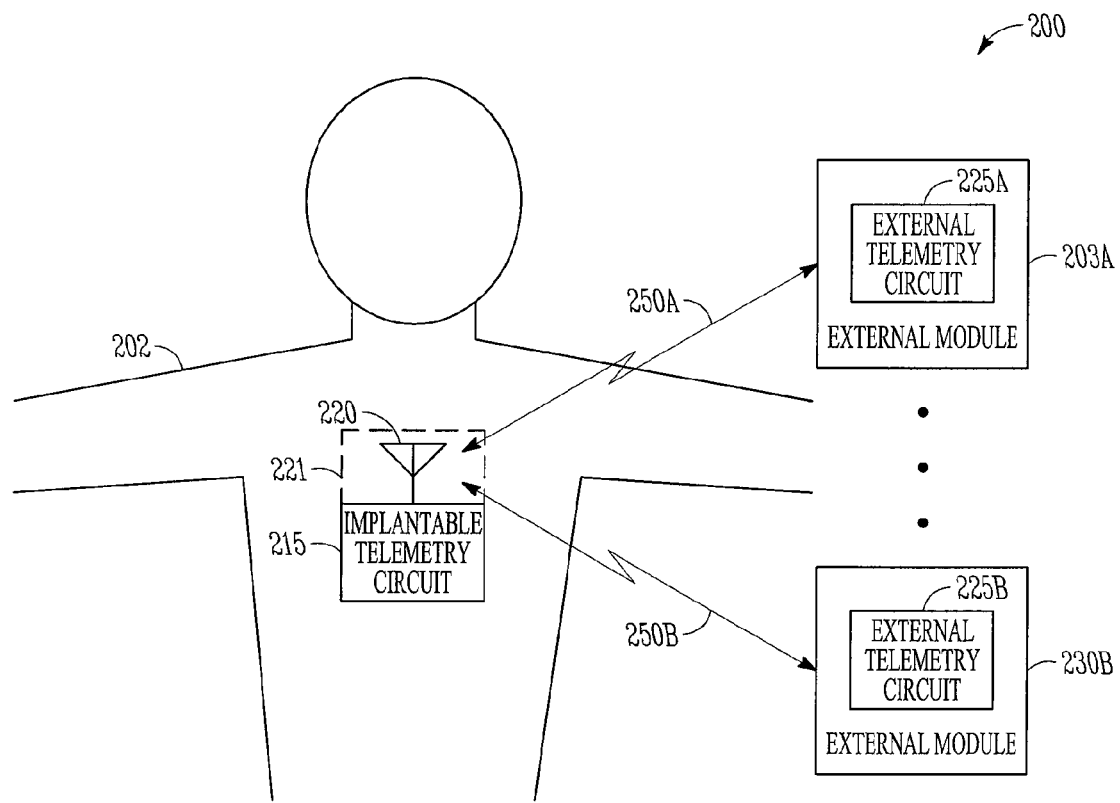
FIG. 2 illustrates generally an example a system including an implantable telemetry circuit and an implantable telemetry antenna in communication with one or more external modules.

FIG. 2 illustrates generally an example a system 200 including an implantable telemetry circuit 215 and an implantable telemetry antenna 220 in communication, such as in RF wireless communication (e.g., using a first RF wireless communication link 250A, a second RF wireless communication link 250B, etc.), with one or more external modules, such as a first external module 230A, a second external module 230B, etc. In an example, the implantable telemetry circuit 215 and the implantable telemetry antenna 220 can be implanted within a patient 202, e.g., subcutaneously, intramuscularly, intrathoracically, or otherwise implanted within the patient 202. In an example, the implantable antenna 220 can be at least partially surrounded by a dielectric compartment 221 comprising a biocompatible dielectric material (e.g., the implantable antenna 220 can be inserted into a cavity within the compartment 221, or the compartment 221 can be formed at least in part by overmolding the antenna 220).

In an example, the first external module 230A or the second external module 230B can include an external telemetry circuit, e.g., a first external telemetry circuit 225A or a second external telemetry circuit 225B, respectively. In certain examples, the first RF wireless communication link 250A can be accomplished using a first range of RF operating frequencies, and the second RF wireless communication link 250B can be accomplished using a second range of RF operating frequencies different than the first range of operating frequencies. In other examples, the first external telemetry circuit 225A or the second external telemetry circuit 225B can use either a first or second operating range of frequencies, or both, for wireless communication. In certain examples, the first external telemetry circuit 225A or the second external telemetry circuit 225B can be electrically connected to one or more external antennas.

Figure 3:
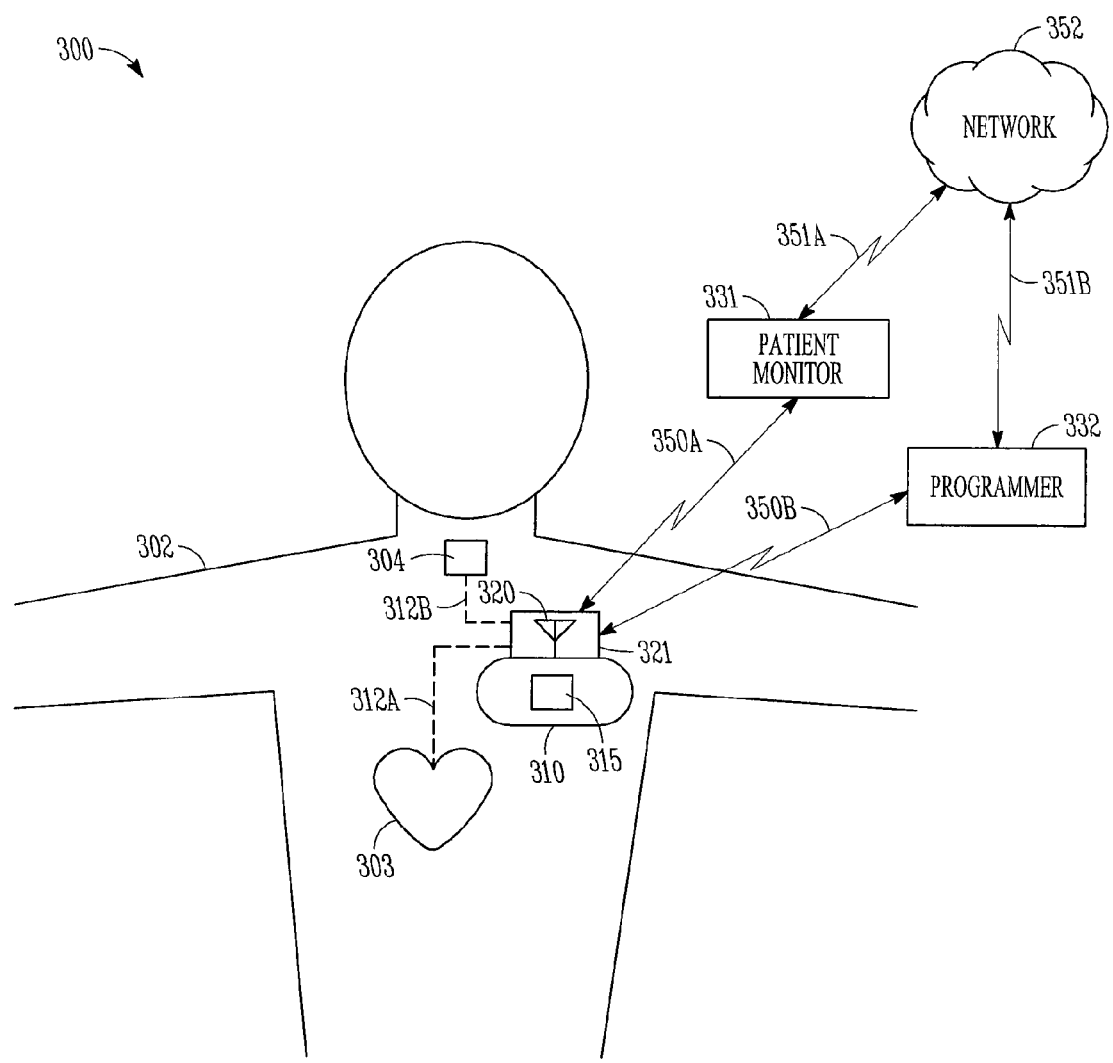
FIG. 3 illustrates generally an example of a system including an implantable medical device (IMD) in communication with at least one of a patient monitor or a programmer.

FIG. 3 illustrates generally an example of a system 300 including an implantable medical device (IMD) 310 in communication, such as in RF wireless communication (e.g., using a first RF wireless communication link 350A, a second RF wireless communication link 350B, etc.), with at least one of a patient monitor 331 or a programmer 332.

In the example of FIG. 3, the IMD 310 can include a implantable telemetry circuit 315 electrically connected to an implantable antenna 320. As similarly discussed with respect to FIG. 2, in some examples, the first RF wireless communication link 350A or the second RF wireless communication link 350B can use more than one RF operating frequency range. In such examples, a single implantable antenna 320 can be configured to operate at two or more RF wireless operating frequencies to support the first RF wireless communication link 350A or the second RF wireless communication link 350B.

According to the example of FIG. 3, the implantable antenna 320 can be at least partially surrounded by a connector block 321. In certain examples, the connector block 321 can be at least partially made of a dielectric material. In various examples, the connector block 321 can also provide an electrical or mechanical connection between the IMD 310 and one or more implantable leads, e.g., a first implantable lead 312A or a second implantable lead 312B. In some examples, the first implantable lead 312A or the second implantable lead 312B can be routed within a patient body 302 to various sites, e.g., to provide a physiologic monitoring of an electrical or a mechanical signal, or to provide a therapy, such as an electrostimulus therapy, a targeted drug release, or other therapy. In the example of FIG. 3, the first implantable lead 312A can be routed to a cardiac tissue site 303 (e.g., an endocardial site, an epicardial site, a site within the myocardium, or other cardiac tissue site) to deliver a therapy, such as a cardiac rhythm management therapy, or the second implantable lead 312B can be routed to a neural target 304 (e.g., a vagal nerve or other neural target) to deliver a therapy, such as a neural stimulation therapy.

In certain examples, the patient monitor 331, the programmer 332, or both the patient monitor 331 and the programmer 332 can be communicatively coupled, e.g., using a first coupling 351A or a second coupling 351B, with a network 352. In an example, the first coupling 351A or the second coupling 351B can include a wired coupling or a wireless coupling. In an example, information can be wirelessly transferred from the IMD 310 to the patient monitor 331 or the programmer 332, and then transferred from the patient monitor 331 or the programmer 332 to the network 352 using the first coupling 351A or using the second coupling 351B.

Figure 4:
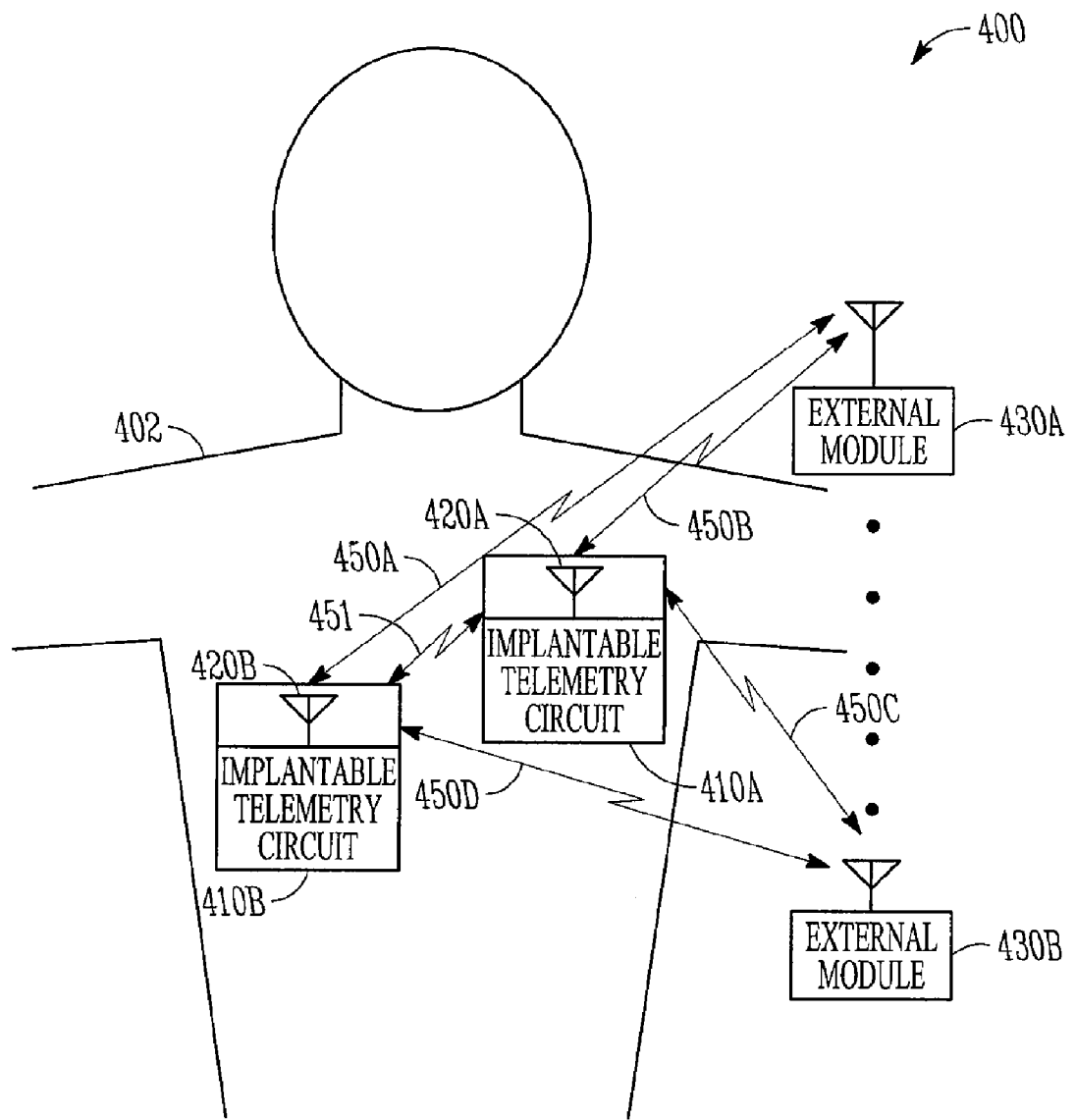
FIG. 4 illustrates generally an example of a system including two or more implantable telemetry circuits in communication with each other, or in communication with one or more external modules.

FIG. 4 illustrates generally an example of a system 400 including two or more implantable telemetry circuits, such as a first implantable telemetry circuit 410A, a second implantable telemetry circuit 410B, etc., in communication, such as in RF wireless communication (e.g., using a RF wireless communication link 451), with each other, or in communication, such as in RF wireless communication (e.g., using a first RF wireless communication link 450A, a second RF wireless communication link 450B, etc.), with one or more external modules, such as a first external module 430A, a second external module 430B, etc.

In an example, the first implantable telemetry circuit 410A or the second implantable telemetry circuit 410B can use the same RF wireless communication scheme for wirelessly coupling to each other (e.g., using the RF wireless communication link 451) as can be used for wirelessly coupling to an external module (e.g., using the first RF wireless communication link 450A or the second RF wireless communication link 450B). In other examples, the first implantable telemetry circuit 410A or the second implantable telemetry circuit 410B can use a first RF wireless operating frequency range for wirelessly coupling to each other, (e.g., using the RF wireless communication link 451), and a second RF wireless operating frequency range for wirelessly coupling to an external module (e.g., using the first RF wireless communication link 450A or the second RF wireless communication link 450B). In certain examples, the RF wireless communication link 451 can include an optical, an acoustic, a magnetic, a body conductive, or other communication link.

In an example, a single first implantable antenna 420A or a single second implantable antenna 420B can be configured to operate at multiple RF wireless communication frequency ranges.

Figure 5A:
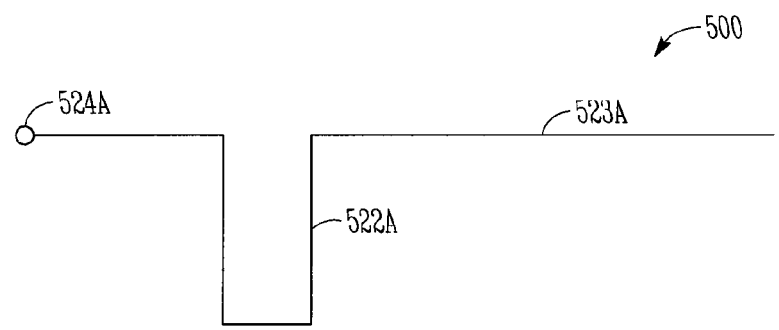
FIGS. 5A-5B illustrate generally examples of at least a portion of an implantable multi-length antenna.
Figure 5B:
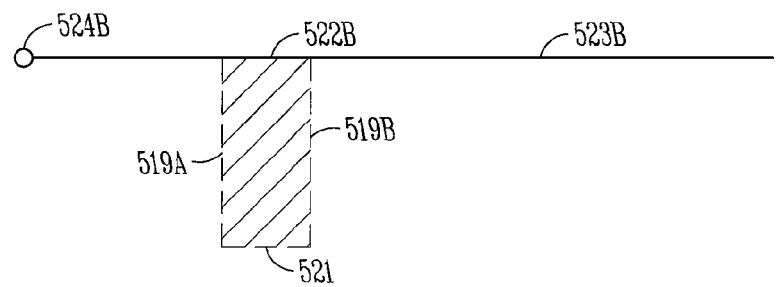

FIGS. 5A-5B illustrate generally examples of at least a portion of an implantable multi-length antenna 500. In the example of FIG. 5A, the implantable multi-length antenna 500 can have a feed segment 524A coupled to a telemetry circuit. A switchback 522A can be coupled to the feed segment 524A, and a non-switchback segment 523A can be coupled to the switchback 522A. In an example, the implantable multi-length antenna 500 can have a physical length and shape as of FIG. 5A. In an example, the implantable multi-length antenna 500 can have an electrical length and shape when operated in a first operating frequency range as of FIG. 5A when the implantable multi-length antenna 500 is substantially surrounded by a first medium (e.g., free space, air, or other medium having a relative dielectric constant approximately equal to 1).

In the example of FIG. 5B, the implantable multi-length antenna 500 of FIG. 5A can be substantially surrounded by a second medium having a higher relative dielectric constant than the first medium. In an example, the implantable multi-length antenna 500 can have a physical length as of FIG. 5A, but can have a shorter electrical length (e.g., the electrical path length along the implantable multi-length antenna 500 corresponding to an RF current resulting in radiation can be shorter than the physical length of the implantable multi-length antenna 500, where the physical length corresponds to the sum of all constituent segment and transition lengths). In an example, when the implantable multi-length antenna 500 is operated in the second medium in a second operating frequency range, capacitive coupling between a first physical switchback segment 519A and a second physical switchback segment 519B can result in a reduction of the electrical length of the implantable multi-length antenna 500 compared to the physical length. In an example, the switchback 522A of FIG. 5A, when substantially surrounded by a second medium having a higher relative dielectric constant than the first medium, can appear electrically as a coupled segment 522B. In this example, the coupled segment 522B can essentially directly (or substantially directly) couple the feed segment 524A to the non-switchback segment 523A, electrically bypassing the intervening switchback.

Thus, the present inventor has, among other things, recognized that a single antenna 500 can appear as two different electrical lengths corresponding to operation in a first frequency range in a first medium and to operation in a second frequency range in a second, different, medium. Further, the present inventor has recognized, among other things, that the physical arrangement of the switchback 522A with respect to the feed segment 524A or the non-switchback segment 523A can be used to alter the electrical length of the implantable multi-length antenna 500. In certain examples, the first operating frequency range and the second operating frequency range can overlap, can be substantially the same, or can be the same.

In certain examples, the feed segment 524A, the switchback 522A, or the non-switchback segment 523A can be etched, stamped, formed, cut, or the like. In some examples, the feed segment 524A, the switchback 522A, or the non-switchback segment 523A can comprise a conductive material, such as platinum, iridium, gold, silver, copper, tin, aluminum, steel, a combination of metals, or other conductive material. In an example, when a portion of the implantable multi-length antenna 500 is configured to be in contact with a biological medium, a bio-compatible conductive alloy can be used, such as platinum-iridium.

In an example, the switchback 522A can include different geometric parameters, such as a switchback cross sectional area, a switchback cross section shape, a spacing between the first switchback segment 519A and the second switchback segment 519B, a shape of a path formed by switchback segment 519A or 519B (e.g., a switchback segment, such as the first switchback segment 519A or the second switchback segment 519B, need not be linear), a length of a transition segment 521, a shape of a path formed by the transition segment 521, a conductor cross sectional area, or other one or more other geometric parameter.

Figure 6A:
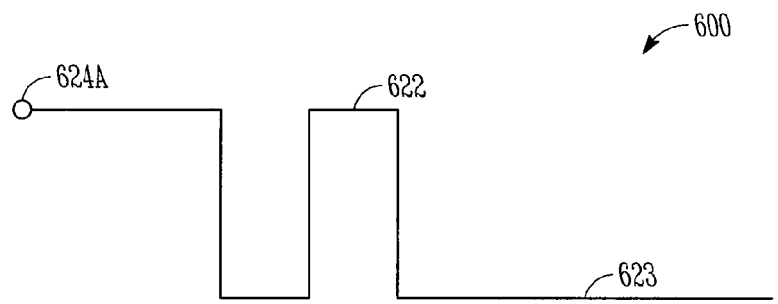
FIGS. 6A-6B illustrate generally examples of physical and electrical lengths of at least a portion of an implantable multi-length antenna when substantially surrounded by two different media.
Figure 6B:
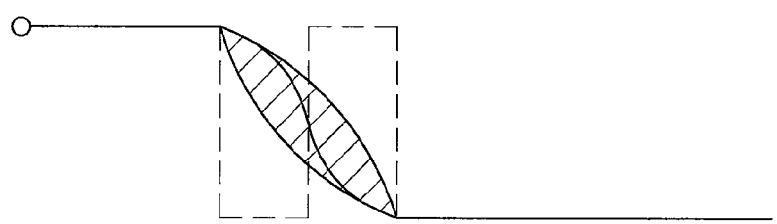

FIGS. 6A-6B illustrate generally examples of physical and electrical lengths of at least a portion of an implantable multi-length antenna 600 when substantially surrounded by two different media.

FIG. 6A illustrates generally an example of an implantable multi-length antenna 600 in a first medium, the implantable multi-length antenna 600 including a feed segment 624A, a switchback segment 622, and a non-switchback segment 623. In an example, the implantable multi-length antenna 600 (having a physical length and shape as of FIG. 6A) can be driven at the feed segment 624A at a first range of frequencies when substantially surrounded by a first medium. In an example, the first medium can include free space, air, or other medium having a low relative dielectric constant (e.g., 1 or approximately 1, etc.). In an example, the switchback 622 can have additional segments, such as one or more other switchback segments, etc., the additional segments electrically connected to the feed segment 624A or to the non-switchback segment 623.

FIG. 6B illustrates generally an example of an implantable multi-length antenna 600 in a second medium. In an example, the second medium can include an implant medium, such as tissue, skin, fat, muscle, bodily fluid, or other implant medium having a relative dielectric constant of more than 1. In an example, the implantable multi-length antenna 600 can have a second electrical length when the implantable multi-length antenna 600 can be used in a second range of frequencies when substantially surrounded by a second, different, medium having a higher relative dielectric constant.

Figure 7A:
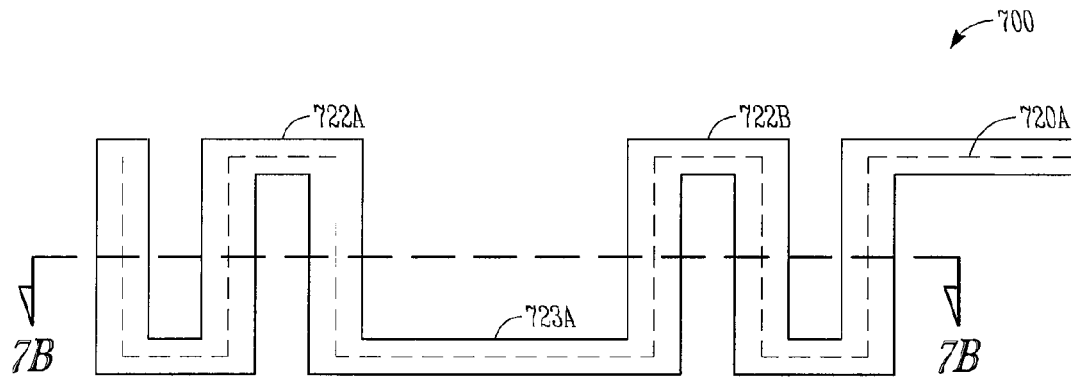
FIGS. 7A-7D illustrate generally examples of top and section views of at least a portion of an implantable multi-length antenna substantially surrounded by two different media.

FIGS. 7A-7D illustrate generally examples of top and section views of at least a portion of an implantable multi-length antenna 700 substantially surrounded by a first medium 702A versus a second medium 702B. FIG. 7A illustrates generally an example of an implantable multi-length antenna 700 in a first medium 702A having a physical length and shape corresponding to a first path 720A, described by a first switchback segment 722A coupled to a first non-switchback segment 723A, and the first non-switchback segment coupled to a second switchback segment 722B.

Figure 7B:
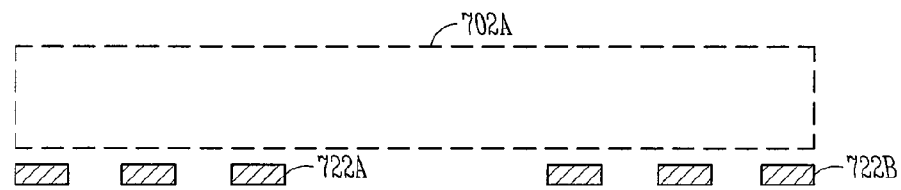

In the examples of FIGS. 7A-7B, when the implantable multi-length antenna 700 is substantially surrounded by a first medium 702A (e.g., air), the implantable multi-length antenna 700 can have an electrical length corresponding to a first path 720A when the antenna is operated in a first range of frequencies.

Figure 7C:
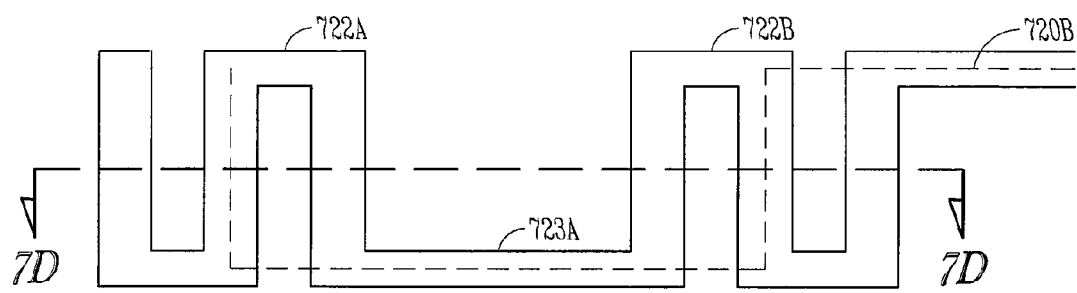
Figure 7D:
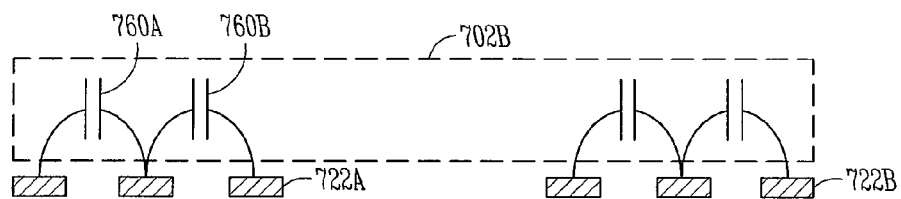

In the examples of FIGS. 7C-7D, when the implantable multi-length antenna 700 is substantially surrounded by a second medium 702B (e.g., a biological medium), the implantable multi-length antenna 700 can have an electrical length corresponding to a second path 720B when the antenna is operated in a second range of frequencies. In some examples, a reduction in electrical length associated with path 720B can occur as a result of an increased electrical flux density in the second medium 702B versus the first medium 702A. In certain examples, the increased electrical flux density can be conceptualized as an increased first capacitance 760A or an increased second capacitance 760B between one or more adjacent segments included in switchback 722A.

Figure 8A:
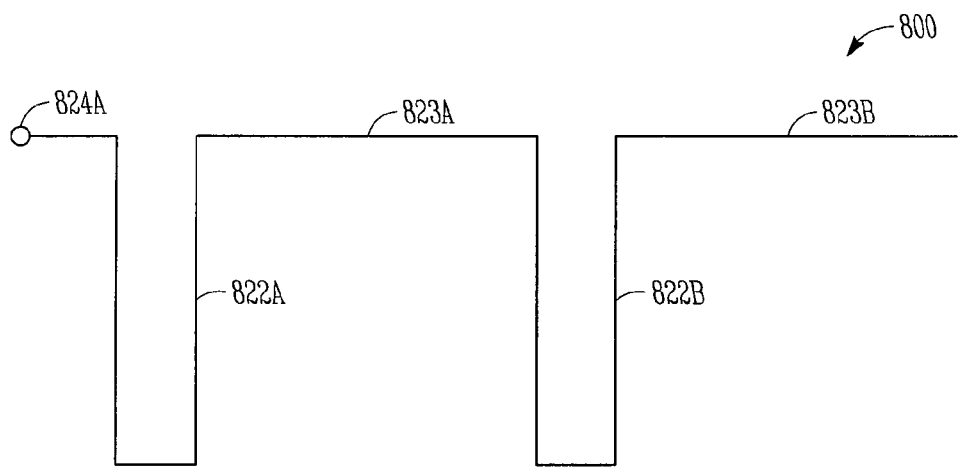
FIGS. 8A-8B, 9A-9B, and 10A-10B illustrate generally examples of physical and electrical lengths of at least a portion of an implantable multi-length antenna substantially surrounded by two different media.
Figure 8B:
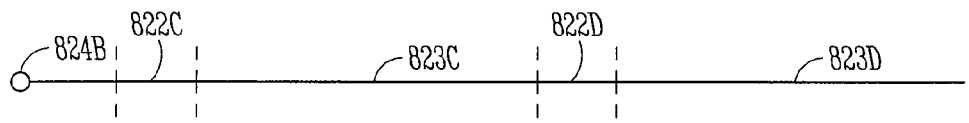

FIGS. 8A-8B illustrate generally examples of physical and electrical lengths of at least a portion of an implantable multi-length antenna 800 substantially surrounded by two different media. In the example of FIG. 8A, the implantable multi-length antenna 800 can have a physical shape and length as formed by a feed segment 824A, a first switchback 822A, a first non-switchback segment 823A, a second switchback 822B, and a second non-switchback 823B. When the implantable multi-length antenna 800 is substantially surrounded by a first medium (e.g., air), the implantable multi-length antenna 800 can have an electrical shape and length corresponding to the physical path of FIG. 8A.

In the example of FIG. 8B, the implantable multi-length antenna 800 can have a physical shape and length as of FIG. 8A, but can have an electrical length and shape formed by a feed segment 824B, a first coupled segment 822C, a first non-switchback segment 823C, a second coupled segment 822D, and a second non-switchback segment 823D. In an example, when the antenna 800 is used in a second range of frequencies substantially surrounded by a second, different, medium having a higher relative dielectric constant, the first switchback 822A can appear electrically as the first coupled segment 822C, and the second switchback 822B can appear electrically as a second coupled segment 822D. The present inventor has recognized, among other things, that having more than one switchback, such as the first switchback 822A and the second switchback 822B, can result in more efficient radiation along the length of the implantable multi-length antenna 800, or can provide a greater range of control over the implantable multi-length antenna 800 input impedance looking into the feed segment 824A.

Figure 9A:
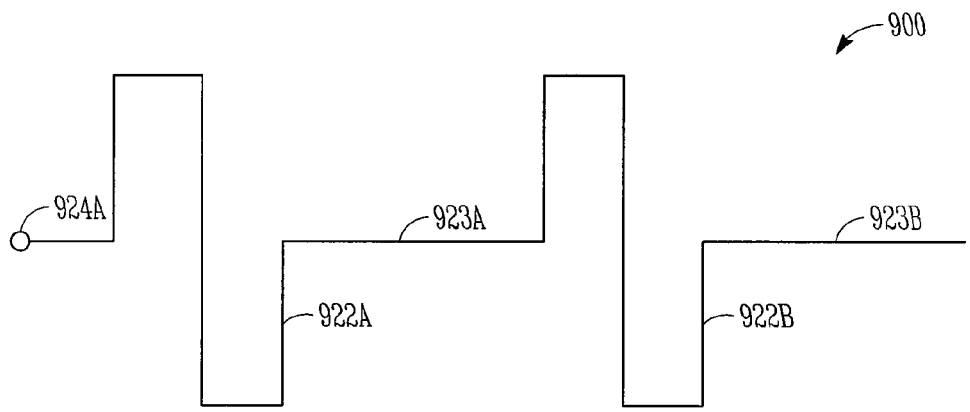
Figure 9B:
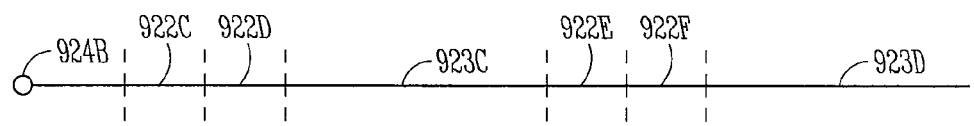

FIGS. 9A-9B illustrate generally examples of physical and electrical lengths of at least a portion of an implantable multi-length antenna 900 substantially surrounded by two different media. In the example of FIG. 9A, a first switchback 922A and a second switchback 922B can deviate in, for example, two directions from a centerline axis formed by a feed segment 924A, a first non-switchback segment 923A, and a non-switchback segment 923B.

In an example, when the implantable multi-length antenna 900 is operated at a second frequency range and terminated in a second medium, the first switchback 922A can appear as multiple coupled segments, such as a first coupled segment 922C and a second coupled segment 922D. Similarly, the second switchback 922B can appear as a third coupled segment 922E and a fourth coupled segment 922F.

In other examples, in the second medium, a feed segment 924B can appear as a slightly different electrical length than the corresponding feed segment 924A in the first medium. Similarly, in the second medium, a non-switchback segment 923C and a non-switchback segment 923D can appear as a slightly different electrical length as the corresponding first non-switchback segment 923A and the non-switchback segment 923B in the first medium . . .

Figure 10A:
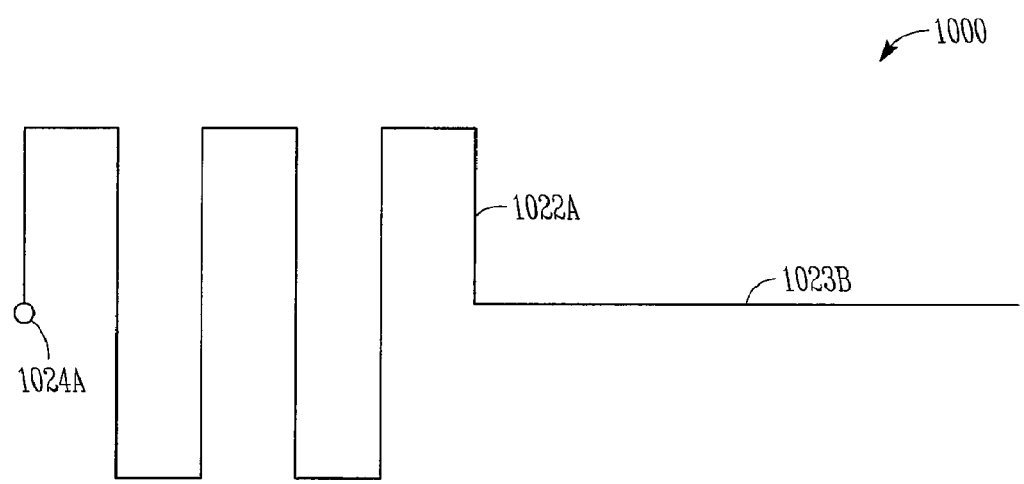
Figure 10B:
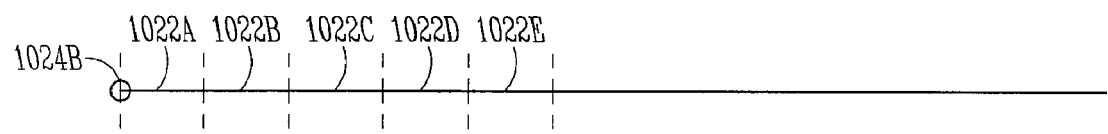

FIGS. 10A-10B illustrate generally examples of physical and electrical lengths of at least a portion of an implantable multi-length antenna 1000 substantially surrounded by two different media. In the example of FIG. 10A, a feed segment 1024A can form part of a switchback segment 1022A. In certain examples, the switchback segment 1022A can include one or more segments or transitions, and can be connected to a non-switchback segment 1023B. In an example, when the implantable multi-length antenna 1000 is operated at a second frequency range in a second medium, the switchback segment 1022A can electrically represent multiple capacitive coupled segments extending from a feed segment 1024B, such as shown by a first coupled segment 1022A, a second coupled segment 1022B, a third coupled segment 1022C, a fourth coupled segment 1022D, or a fifth coupled segment 1022E in the example of FIG. 10B.

The present inventor has, among other things, also recognized that at lower frequencies (e.g., below the frequency range where capacitive coupling can dominate), the switchback segment 1022A can have enhanced inductance and can be used to provide a loading effect (e.g., to alter the input impedance of the implantable multi-length antenna 1000 looking into the feed segment 1024A in order to provide an improved impedance match between the implantable multi-length antenna 1000 and a driving or receiving telemetry circuit).

Figure 11:
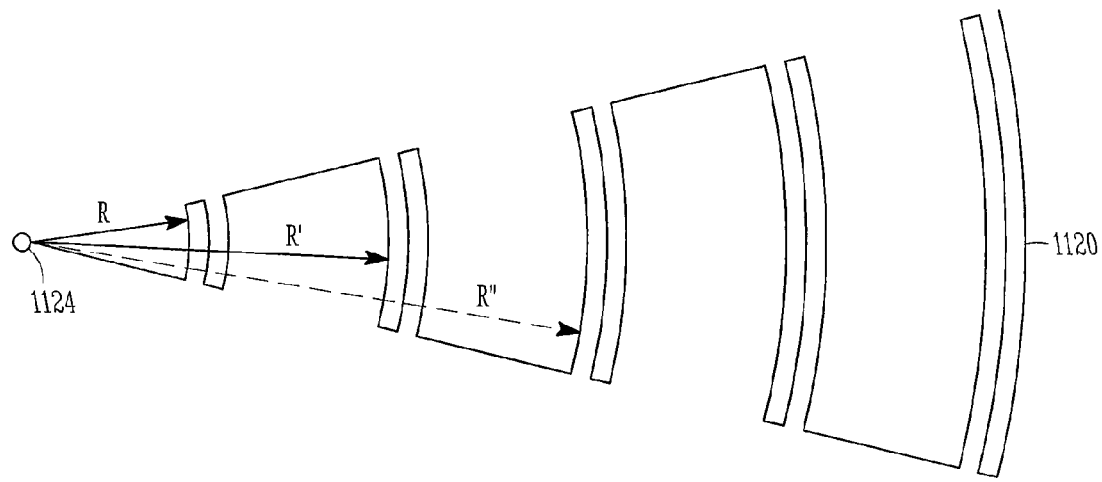
FIG. 11 illustrates generally an example of at least a portion of an implantable multi-length antenna having a tapered width.

FIG. 11 illustrates generally an example of at least a portion of an implantable multi-length antenna 1120 having a tapered width. In an example, the implantable multi-length antenna 1120 can expand in width linearly (e.g., with respect to a centerline axis) as it extends from a feed segment 1124. In other examples, the shape of the taper can be non-linear (e.g., exponential, sinusoidal, in conformance to a shape of a dielectric housing, in conformance to a shape of an IMD housing, biased more on one side of a centerline axis, or other shape or configuration). In some examples, the shape of the taper can be inverted with respect to the previously described examples (e.g., starting wider at the feed segment 1124 and narrowing along the length of the implantable multi-length antenna 1120).

Generally, a relative dielectric constants of a biological medium can vary significantly. In certain examples, one or more bodily fluids can have a relative dielectric constant over 50, and muscle tissue can have a relative dielectric constant over 20. In an example, the implantable multi-length antenna 1120 can be applied in a variety of different biological mediums, including a bodily fluid (e.g., blood, a digestive juice, a lymph, water, or other bodily fluid), muscle tissue, bone tissue, fat tissue, skin, or other biological medium.

The present inventor has recognized, among other things, that when an antenna is locally surrounded by a material having a lower relative dielectric constant (e.g., such as by a coating or a surrounding dielectric housing), a tapered shape can help to more gradually match the antenna to a spatial impedance of a higher relative dielectric constant medium, and, in certain examples, can provide more efficient radiation into the higher relative dielectric constant medium.

The present inventor has recognized, among other things, that a gradual shift in feature size can be made on the implantable multi-length antenna 1120, a usable bandwidth can be increased (e.g., size of an operating frequency range).

In an illustrative example, TECOTHANE™ polymer material can have a relative dielectric constant of approximately 4.4 over a range of frequencies. Generally, a biological medium can have a relative dielectric constant greater than 5. In certain examples, an IMD connector block can be made from TECOTHANE™, and can surround part or all of the implantable multi-length antenna 1120. In various examples, the implantable multi-length antenna 1120 can be wider in a region where the connector block is thicker, and the implantable multi-length antenna 1120 can be narrower in a region where the connector block is thinner, such as in order to help match the implantable multi-length antenna 1120 to an effective relative dielectric constant comprising a combination of the TECOTHANE™ and the biological medium.

Generally, the desired antenna length in a given medium can be inversely proportional to the square root of the effective relative dielectric constant as seen by the antenna when surrounded by one or more media. The present inventor has recognized, among other things, that a tradeoff can exist between proximity to an IMD housing and radiation efficiency, when the IMD housing includes a conductor. In an example, as the implantable multi-length antenna 1120 is located more closely to a conductive IMD housing, the degree of impedance stability of the implantable multi-length antenna 1120 can increase (e.g., become less sensitive to the medium surrounding the IMD). In other examples, as the implantable multi-length antenna 1120 is located more closely to the conductive IMD housing, the effective dielectric constant as seen by the antenna can be more stable. However, as the implantable multi-length antenna 1120 is located more closely to a conductive IMD housing, the implantable multi-length antenna 1120 can radiate less efficiently, in certain examples, because the IMD housing can "short out" the antenna radiation, or because the implantable multi-length antenna 1120 can appear electrically longer because the effective relative dielectric constant seen by the implantable multi-length antenna 1120 can be lower.

Figure 12:
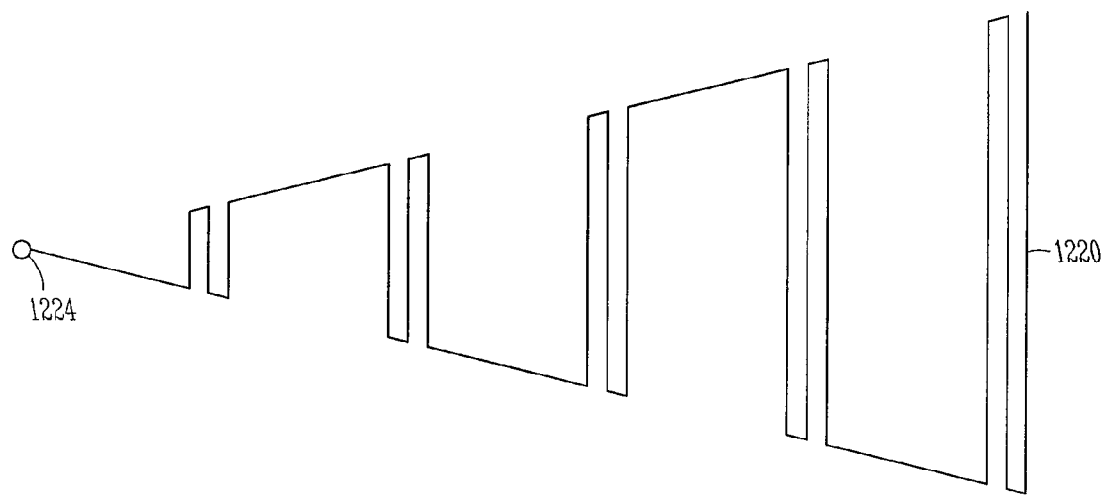
FIG. 12 illustrates generally an example of at least a portion of an implantable multi-length antenna having a tapered width and one or more arc-shaped switchback segments.

FIG. 12 illustrates generally an example of at least a portion of an implantable multi-length antenna 1220 having a tapered width and one or more arc-shaped switchback segments extending from a feed segment 1224. Similar to the example of FIG. 11 with respect to tapering, the present inventor has recognized, among other things, that having one or more segments or transitions of the implantable multi-length antenna 1220 arranged at right angles (e.g., perpendicular to one another) can enhance a radiation efficiency of the implantable multi-length antenna 1220 (e.g., can enhance a radiation resistive component of an impedance of the implantable multi-length antenna 1220). In the example of FIG. 12, one or more switchback segments can be arc-shaped to allow approximately right angles where the one or more switchback segments are connected to one or more non-switchback segments.

Figure 13A:
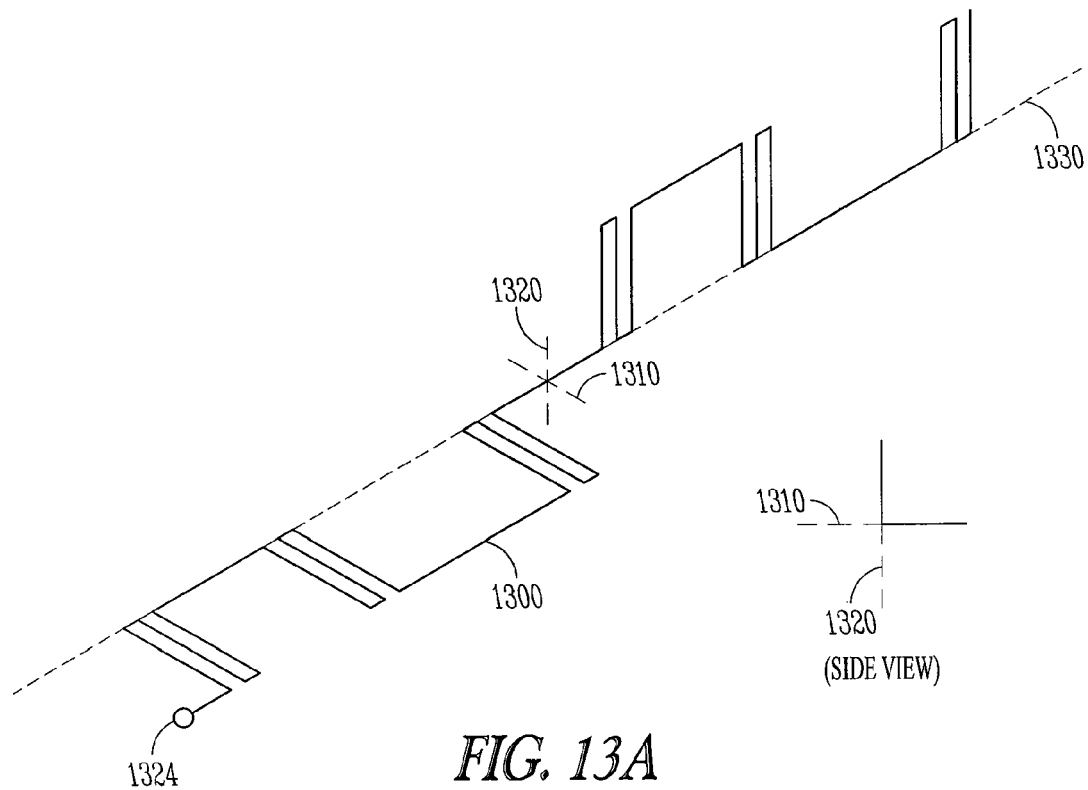
FIGS. 13A-13B illustrate generally examples of at least a portion of an implantable multi-length antenna having at least two switchback segments positioned in different planes.

FIG. 13A illustrates generally an example of at least a portion of an implantable multi-length antenna 1300 having at least two switchback segments positioned in different planes. In the example of FIG. 13A, the implantable multi-length antenna 1300 can be driven at a feed segment 1324 leading into one or more first switchback segments located in a first plane. In an example, the first plane can be formed by a first axis 1330 located along the implantable multi-length antenna 1300 and a line forming a second axis 1310 perpendicular to the first axis 1330. In an example, a second plane, different than the first plane, can be formed by the first axis 1330 and a third axis 1320. In certain examples, one or more second switchback segments located in the second plane can be connected to the first switchback segments located in the first plane. In an example, the second plane can be normal (perpendicular) to the first plane. In other examples, the second plane can be different than the first plane, but need not be at a right angle.

The present inventor has recognized, among other things, that the implantable multi-length antenna 1300 can exhibit greater directivity (e.g., less isotropic radiation pattern) when constrained to a single plane than when having switchback segments in different planes.

In an example, isotropic radiation can be desired to improve a reliability of RF wireless communication between an IMD and another IMD or an external device (e.g., to prevent communication drop-outs due to device orientation, dead spots, etc.

In certain examples, one or more switchback or non-switchback segments can be located in more than one plane to increase a radiation pattern uniformity (e.g., to provide radiation in all directions more uniformly). Further, in certain examples, the whole implantable multi-length antenna 1300, or at least a portion of the implantable multi-length antenna 1300, can bend along the main axis (e.g., rotate, etc.) to an angle other than a right angle or other than perpendicular to the main axis. In an example, this bending can provide a more distribution radiation directions than just having the switchbacks in two perpendicular planes.

Figure 13B:
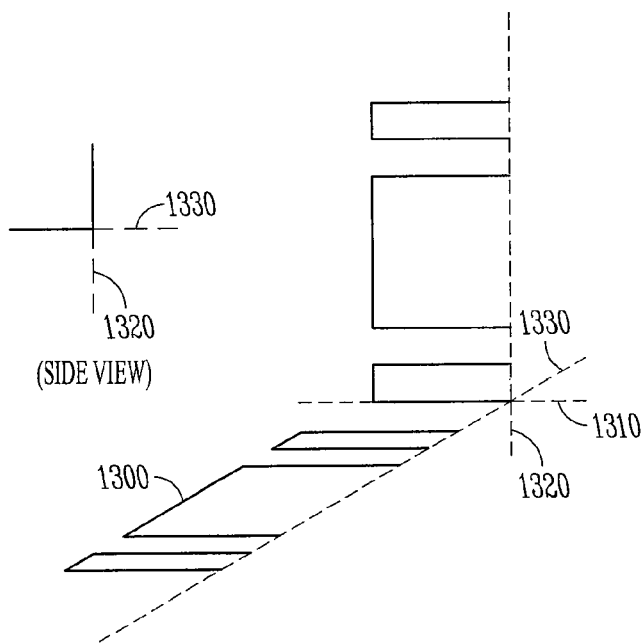

FIG. 13B illustrates generally an example of at least a portion of an implantable multi-length antenna 1300 having at least two switchback segments positioned in different planes. In an example, the first plane can be formed by a first axis 1330 located along the implantable multi-length antenna 1300 and a line forming a second axis 1310 perpendicular to the first axis 1330. In an example, a second plane, different than the first plane, can be formed by the second axis 1310 and a third axis 1320. In certain examples, one or more second switchback segments located in the second plane can be connected to the first switchback segments located in the first plane. In an example, the second plane can be normal (perpendicular) to the first plane. In other examples, the second plane can be different than the first plane, but need not be at a right angle.

Figure 14:
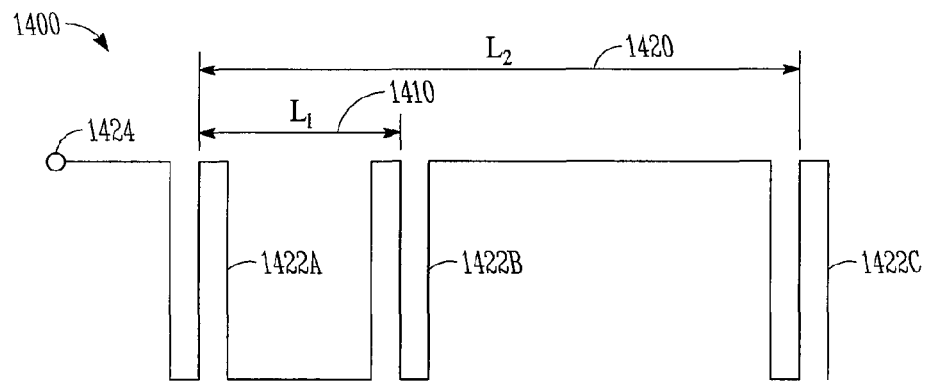
FIG. 14 illustrates generally an example of at least a portion of an implantable multi-length antenna having at least two different distances between adjacent switchback configurations.

FIG. 14 illustrates generally an example of at least a portion of an implantable multi-length antenna 1400 having at least two different distances between adjacent switchback configurations. In the example of FIG. 14, a first length $L_1$ 1410 defines a distance between a first switchback 1422A and a second switchback 1422B. The first length $L_1$ 1410 can correspond to a resonant frequency associated with a first operating frequency range when the implantable multi-length antenna 1400 is driven at a feed segment 1424. In an example, $L_1$ can be an integer multiple of approximately a quarter wavelength. Similarly, a second length $L_2$ 1420 can be defined by a distance between the first switchback 1422A and a third switchback 1422C, corresponding to a second, different, operating frequency range, or resonance. In other examples, at least one of the first length $L_1$ 1410 or the second length $L_2$ 1420 can be significantly different than the quarter wavelength.

Figure 15A:
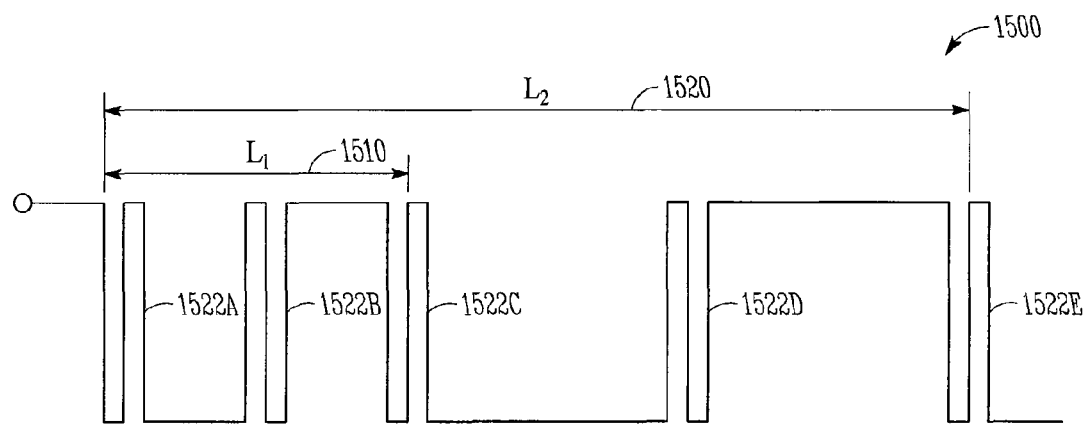
FIGS. 15A-15B illustrate generally examples of physical and electrical lengths of at least a portion of an implantable multi-length antenna having at least two different distances between adjacent switchback configurations.
Figure 15B:

FIGS. 15A-15B illustrate generally examples of physical and electrical lengths of at least a portion of an implantable multi-length antenna 1500 having at least two different distances between adjacent switchback configurations.

The present inventor has recognized, among other things, that a multi-length antenna can be configured to operate in at least two different media, and can also be operated in two different frequency ranges in the at least two different media using more than one non-switchback segments of varying length between one or more switchback.

FIG. 15A illustrates generally a first electrical shape and length of an implantable multi-length antenna 1500 having multi-frequency capability in a first medium. Similar to the example of FIG. 14, a first length $L_1$ 1510 can define a region corresponding to a first "pitch" between adjacent switchbacks, such as between a first switchback 1522A, a second switchback 1522B, and a third switchback 1522C. Similarly, a second length $L_2$ 1520 can define a region corresponding to a second "pitch" between adjacent switchbacks, such as between the first switchback 1522A, the second switchback 1522B, the third switchback 1522C, a fourth switchback 1522D, and a fifth switchback 1522E. In an example, at least one of the first length $L_1$ 1510 or the second length $L_2$ 1520 can establish a first or a second operating frequency range for the implantable multi-length antenna 1500 in the first medium.

In the example of FIG. 15B, the implantable multi-length antenna 1500 is surrounded in a second medium having a higher relative dielectric constant than the first medium. In an example, the switchback segments from FIG. 15A can capacitively couple in the second medium. In certain examples, the effective electrical length of the implantable multi-length antenna 1500 shown in FIG. 15A can appear, in the second medium, as the shape and length shown in FIG. 15B. In an example, the length of the implantable multi-length antenna 1500 in the first medium and the effective electrical length of the implantable multi-length antenna 1500 in the second medium can be used to provide communication in the first medium and in the second medium.

FIG. 16 illustrates generally an example of a first radiation efficiency 1630 of an implantable multi-length antenna substantially surrounded by a first medium, and a second radiation efficiency 1640 of an implantable multi-length antenna substantially surrounded by a second medium. In an example, a radiation efficiency (e.g., "η") can be defined as the ratio of radiated electromagnetic energy versus the energy supplied to an implantable antenna by a connected telemetry circuit.

On a vertical axis, a radiation efficiency 1610, ("η"), of the implantable multi-length antenna can be plotted versus frequency 1620. In an example, an implantable multi-length antenna can provide a first radiation efficiency peak 1635 or a second radiation efficiency peak 1645 above a specified minimum radiation efficiency 1615, ("$\eta_{MIN}$"). In certain examples, a first operating frequency range 1637 can be defined by a region where the first radiation efficiency 1635 is at or above the specified minimum radiation efficiency 1615. In other examples, a mid-band frequency 1650, $f_c$, can be defined approximately where the first radiation efficiency peak 1635 occurs.

Similarly, in the example of FIG. 16, a second radiation efficiency peak 1645 can occur at or approximately the mid-band frequency 1650. In certain examples, a second operating frequency range 1647 can be defined by a region where the second radiation efficiency 1640 is at or above the specified minimum radiation efficiency 1615.

In an example, the first radiation efficiency 1630 can correspond to an implantable multi-length antenna surrounded by a first medium, and the second radiation efficiency 1640 can correspond to an implantable multi-length antenna surrounded by a second medium having a greater relative dielectric constant than the first medium (e.g., the first medium can include free space or air, and the second medium can include a biological medium), or vice versa. The present inventor has recognized, among other things, that even if the second radiation efficiency 1640 is generally much lower than the first radiation efficiency 1630, a usable second operating frequency range 1647 above the specified minimum radiation efficiency 1615 can exist using a single physical antenna length. In certain examples, the second operating frequency range 1647, or the second radiation efficiency peak 1645 can be greater, or larger, respectively, than a corresponding single-length antenna omitting a capacitive-coupled switchback segment, where a corresponding single-length antenna substitutes a non-switchback segment for the switchback segment.

In an example, the second radiation efficiency peak 1645 can occur at a different frequency than the first radiation efficiency peak 1635 (e.g., the multi-length antenna can be physically arranged to provide the first operating frequency range 1637 in air and the second operating frequency range 1647 in a biological medium.)

In some examples, at least one of the first radiation efficiency peak 1635 or the second radiation efficiency peak 1645 can occur when a multi-length antenna is operated at or near a resonant frequency.

Figure 17:
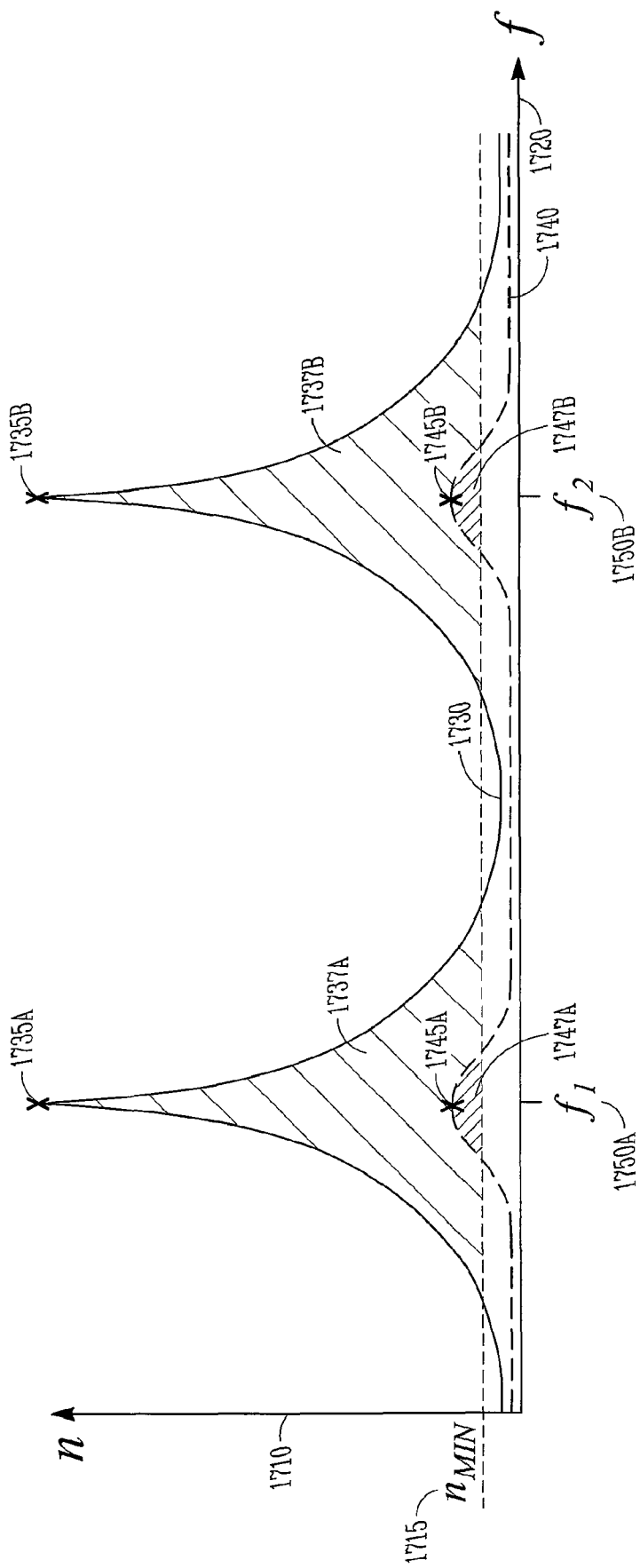
FIG. 17 illustrates generally an example of a radiation efficiency of an implantable multi-length antenna having multi-frequency capability substantially surrounded by two different media.

FIG. 17 illustrates generally a conceptualized example of a first radiation efficiency 1730 of an implantable multi-length antenna having multi-frequency capability substantially surrounded by a first medium, and a second radiation efficiency 1740 of an implantable multi-length antenna having multi-frequency capability substantially surrounded by a second medium.

In the example of FIG. 17, the implantable multi-length antenna can have a first frequency radiation efficiency peak 1735A in the first medium at or near a first mid-band frequency 1750A, and a second frequency radiation efficiency peak 1735B in the first medium at or near a second mid-band frequency 1750B. In an example, a first operating frequency range 1737A in the first medium can be specified by defining a region in which a first radiation efficiency 1730 is greater than or equal to a specified minimum radiation efficiency 1715. Similarly, a second operating frequency range 1737B in the first medium can be specified by defining a region at which the first radiation efficiency 1730 is greater than or equal to a specified minimum radiation efficiency 1715.

In an example, the implantable multi-length antenna can have a first frequency radiation efficiency peak 1745A in the second medium at or near a first mid-band frequency 1750A, and a second frequency radiation efficiency peak 1745B in the second medium at or near a second mid-band frequency 1750B.

In an example, a first operating frequency range 1747A in the second medium can be specified by defining a first lower frequency limit, $f_{1L}$, in the second medium and a first upper frequency limit, $f_{1H}$, in the second medium at which the first radiation efficiency 1740 is greater than or equal to the specified minimum radiation efficiency 1715. Similarly, a second operating frequency range 1747B in the second medium can be specified by defining a second lower frequency limit, $f_{2L}$, in the second medium and a second upper frequency limit, $f_{2H}$, in the second medium at which the first radiation efficiency 1740 is greater than or equal to the specified minimum radiation efficiency 1715.

In an example, when substantially surrounded by the second medium (e.g., implanted in tissue), the implantable multi-length antenna can be configured to operate over the first operating frequency range 1747A of approximately $f_{1L}$=375 MHz. and $f_{1H}$=425 MHz, having the first mid-band frequency 1750A of approximately $f_1$=400 MHz. Further, in this example, the implantable multi-length antenna can be configured to operate over the second frequency range 1747B of approximately $f_{2L}$=850 MHz. and $f_{2H}$=900 MHz., having the second mid-band frequency 1750B of approximately $f_2$=875 MHz.

In another example, the implantable multi-length antenna can be configured to operate over the first operating frequency range 1747A of approximately $f_{1L}$=900 MHz. and $f_{1H}$=950 MHz., having the first mid-band frequency 1750A of approximately $f_1$=925 MHz. Further, in this example, the multi-frequency antenna can be configured to operate over the second frequency range 1747B of approximately $f_{2L}$=2.4 GHz.

and $f_{2H}$=2.5 GHz., having the second mid-band frequency 1750B of approximately $f_2$=2.45 GHz.

In other examples, the multi-frequency antenna can be substantially surrounded by the first medium or the second medium, and can be configured to operate in at least two of:

(1) a Short Range Device (SRD) band range (e.g., 862-870 MHz.);

(2) a first Industrial-Scientific-Medical (ISM) band range (e.g., 902-928 MHz.);

(3) a second Industrial-Scientific-Medical (ISM) band range (e.g., 2.4-2.5 GHz.);

(4) a Medical Implant Communications Service (MICS) band range (e.g., 402-405 MHz.); or (5) one or more other frequency band ranges configured for communication between an IMD and one or more other implantable or external devices.

FIG. 18 illustrates generally an example of at least a portion of a system 1800 including a telemetry circuit 1815 electrically connected to an implantable multi-length antenna 1820. In an example, the telemetry circuit 1815 can include a telemetry transceiver 1817 coupled to a matching circuit 1816 using a first RF input/output line 1820A. In an example, the telemetry transceiver 1817 can be coupled to the matching circuit 1816 using a first RF input/output line 1820A.

In an example, the telemetry circuit 1815 can be partially or completely enclosed in an IMD housing 1810. In certain examples, the IMD housing 1810 can be made of a conductive material, such as a metal, a combination of metals, a biocompatible metal, etc. In an example, the telemetry transceiver 1817 can be coupled to the telemetry circuit 1815 using a first connection 1840A. Further, the telemetry circuit 1815 can be electrically connected to the IMD housing 1810 using a second connection 1840B. In an example, an RF current return path can be provided from the telemetry transceiver 1817 to the telemetry circuit 1815 using the first connection 1840A, and from the telemetry circuit 1815 to the IMD housing 1810 using the second connection 1840B.

In an example, the telemetry circuit 1815 can be coupled to the implantable multi-length antenna 1820 using a second RF input/output line 1820B. In certain examples, the second RF input/output line 1820B can penetrate the IMD housing 1810 to couple the telemetry circuit 1815 and the implantable multi-length antenna 1820. In other examples, at least a portion of the implantable multi-length antenna 1820 or the telemetry circuit 1815 can be contained in the IMD housing 1810, in a dielectric or other compartment coupled to the IMD housing 1810, or outside of the IMD housing 1810.

In an example, the implantable multi-length antenna can include a first switchback 1823A and a second switchback 1823B. In other examples, one or both of the first switchback 1823A or the second switchback 1823B can be omitted from the implantable multi-length antenna 1820, and a similar length non-switchback segment can be substituted. In this example, the implantable multi-length antenna 1820 can provide a capacitive load to the telemetry circuit 1815 (e.g., at the second RF input/output line 1820B looking into the implantable multi-length antenna 1820 through the feed-through 1818). In certain examples, the matching circuit 1816 (e.g., including an impedance matching element) can be included to compensate for an excess inductance or capacitance of the implantable multi-length antenna 1820. In the example of an omitted first switchback 1822A or second switchback 1822B, the impedance matching element 1816 can include a discrete inductor. In the example of FIG. 18, the inclusion of a first switchback 1822A or a second switchback 1822B can reduce the value of or eliminate the need for the impedance matching element 1816 within the telemetry circuit 1815.

In certain examples, a conjugate impedance match between the first RF input/output line 1820A and the implantable multi-length antenna 1820 can provide or can enhance a power transfer to the implantable multi-length antenna 1820 at a given frequency. In an example, the real portion of the input impedance of the implantable multi-length antenna 1820 can include a real value of 50 Ohms. In this example, when the first switchback 1822A or the second switchback 1822B is omitted from the implantable multi-length antenna 1820 and a similar length non-switchback segment is substituted, the implantable multi-length antenna 1820 can include an imaginary portion of an impedance of approximately −j20 Ohms (e.g., the implantable multi-length antenna 1820 can present a capacitive load to the telemetry circuit 1815).

In certain examples, a conjugate impedance match can be provided or otherwise configured between the telemetry circuit 1815 and the implantable multi-length antenna 1811, using, for example, the phase contribution of the first RF input/output line 1819A and the second RF input/output line 1819B, the impedance matching element 1816 can provide an inductive contribution to the output impedance of the telemetry transceiver 1817 of approximately +j20 Ohms to approximately cancel out the capacitance of the implantable multi-length antenna 1820.

In another example, at least one of the first switchback 1822A or the second switchback 1822B can compensate for the capacitance of the implantable multi-length antenna 1820 to provide an approximately real input impedance (e.g., without an imaginary component) looking into the implantable multi-length antenna 1820 at the feed-through 1818. In this example, the impedance matching element 1816 can be omitted, or can be replaced with a purely resistive matching element (e.g., a substantially resistive mismatch can exist between the implantable multi-length antenna 1820 and an output impedance of the telemetry transceiver 1817).

In an example, when the implantable multi-length antenna 1820 is operated at multiple frequencies, the matching element 1816 can be used to provide an enhanced conjugate match at a first operating frequency range, and the impedance matching contribution from the first switchback 1822A or the second switchback 1822B can be minimal in the first operating frequency range. Similarly, in an example, an impedance matching contribution from the matching element 1816 can be minimal in a second operating frequency range, and the impedance matching contribution from the first switchback 1822A or the second switchback 1822B can be used to provide an enhanced conjugate match (e.g., if the matching element 1816 is operated at its unity-power factor self-resonant frequency, it can appear as a resistive element rather than as a capacitor or an inductor).

In one example, when the implantable multi-length antenna 1820 is operated at multiple frequencies, the matching element 1816 can be controllably switched out of the transmit and receive path between the first RF input/output line 1819A and the second RF input/output line 1819B. In certain examples, one or more values for the matching element 1816 can be selected to provide an approximate conjugate match at more than one specified range of operating frequencies, or in more than one medium surrounding the implantable multi-length antenna 1820.

In certain examples, the implantable telemetry circuit 1815 can be configured as a transmitter, a receiver, or both. Generally, the principles described in connection with bi-directional wireless information transfer between an implantable antenna and another wireless device can also apply to uni-directional wireless information transfer. According to a physical principal of reciprocity, antenna behavior can be generally reciprocal (e.g., an antenna physically arranged as a transmitting antenna can also act as a receiving antenna having similar characteristics).

FIG. 19 illustrates generally an example of a process 1900 including, at 1905, wirelessly transferring information electromagnetically at a first operating frequency range in a first medium and wirelessly transferring information electromagnetically at a second operating frequency range in a second medium.

In an example, the first medium (e.g., free space, air, or one or more other mediums having a relative dielectric constant approximately equal to 1) can be different than the second medium (e.g., a biological medium, bodily fluid, skin tissue, fat tissue, muscle tissue, organ tissue, bone, or one or more other biological mediums). In an example, the first operating frequency range can be substantially equal to or the same as the second operating frequency range.

In other examples, the implantable multi-length antenna can be configured to appear electrically as a first length ("the first electrical length") in the first medium and to appear electrically as a second length ("the second electrical length") in the second medium. In an example, the first electrical length can include a length different than the second electrical length. In certain examples, the first operating frequency range can be dependent at least in part upon (e.g., tuned or otherwise configured using) the first electrical length, and the second operating frequency range can be dependent at least in part upon (e.g., tuned or otherwise configured using) the second electrical length.

FIG. 20 illustrates generally an example of a Smith Chart illustrating a relationship between an effective impedance of an antenna and a relative permittivity of a medium. In an example, a first impedance 1901 at a first frequency ($F_0$) in a first medium having a first relative permittivity ($E_{r1}$) can be plotted against a second impedance 1902 at the first frequency ($F_0$) in a second medium having a second relative permittivity ($E_{r2}$). In certain examples, as long as the impedance of the antenna in the first medium and the second, different, medium has the same impedance, one matching network (or compensation network) can be used to maximize radiation in the first medium and in the second medium, such as at a point of common impedance (e.g., as illustrated in FIG. 20).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable telemetry circuit;
an implantable multi-length antenna electrically connected to the implantable telemetry circuit and configured to wirelessly transfer information electromagnetically at a specified first operating frequency range when in a first medium and at a specified second operating frequency range when in a different second medium, the implantable multi-length antenna including:
a first non-switchback segment;
a first switchback, electrically connected to the first non-switchback segment, the first switchback comprising first and second switchback segments; and
a second non-switchback segment electrically connected to the first switchback;
wherein the implantable multi-length antenna is configured to appear electrically as a first electrical length when in the first medium and as a different second electrical length when in the second medium;
wherein the second electrical length in the second medium is less than a physical length of the implantable multi-length antenna due at least in part to a capacitive coupling of the first switchback segment and the second switchback segment when in the second medium; and
wherein the first operating frequency range is specified using the first electrical length and the second operating frequency range is specified using the second electrical length.

2. The system of claim 1, wherein the first operating frequency range is substantially equal to the second operating frequency range.

3. The system of claim 1, wherein the first operating frequency range includes at least one of:
- a medical implant communication service (MICS) range from approximately 402 MHz to 405 MHz;
- a short range device (SRD) range from approximately 862 MHz to 870 MHz;
- a first industrial scientific and medical (ISM) range from approximately 902 MHz to 928 MHz; or
- a second ISM range from approximately 2400 MHz to 2500 MHz.

4. The system of claim 1, wherein the first medium includes a dielectric material having a relative dielectric constant of approximately 1 and the second medium includes a dielectric material having a relative dielectric constant greater than or equal to 5.0.

5. The system of claim 4, wherein the first medium is air and the second medium is a biological medium, wherein the biological medium includes at least one of bodily fluid, skin tissue, fat tissue, muscle tissue, organ tissue, or bone.

6. The system of claim 1, wherein the first electrical length of the implantable antenna when in the first medium is different than the second electrical length of the implantable antenna when in the second medium due at least in part to a difference in a relative dielectric constant of the first medium and a relative dielectric constant of the second medium.

7. The system of claim 1, wherein at least one of the first switchback segment or the second switchback segment comprise an arc shaped segment having a constant radius from a specified position.

8. The system of claim 1, wherein the implantable multi-length antenna includes:
- a second switchback electrically connected to the second non-switchback segment, the second switchback located a first distance from the first switchback;
- a third non-switchback segment electrically connected to the second switchback, the third non-switchback segment approximately parallel to the first axis; and
- a third switchback electrically connected to the third segment, the third non-switchback switchback located a different second distance from the second switchback.

9. The system of claim 8, wherein the implantable multi-length antenna is configured to wirelessly transfer information electromagnetically at a specified third operating frequency range when in the first medium and at a specified fourth operating frequency range when in the second medium;
- wherein the third operating frequency range is different than the first operating frequency range and the fourth operating frequency range is different than the second operating frequency range;
- wherein the first operating frequency range and the second operating frequency range are specified using the first distance between the first switchback and the second switchback; and
- wherein the third operating frequency range and the fourth operating frequency range are specified using the second distance between the second switchback and the third switchback.

10. The system of claim 1, wherein the first non-switchback segment is positioned approximately parallel to a first axis;
- wherein the first and second switchback segments comprising the first switchback are approximately parallel to a second axis; and
- wherein the second non-switchback segment is approximately parallel to the first axis.

11. The system of claim 10, wherein the second axis is substantially perpendicular to the first axis; and
- wherein the implantable multi-length antenna includes a second switchback electrically connected to the second non-switchback segment, wherein the first switchback is positioned in a plane defined by the first axis and the second axis, wherein the second switchback is positioned in a plane defined by the first axis and a third axis, and wherein the third axis is substantially perpendicular to the first axis and different than the second axis.

12. A method comprising:
- using an implantable multi-length antenna, wirelessly transferring information electromagnetically at a specified first operating frequency range when the implantable multi-length antenna is in a first medium and a specified second operating frequency range when the implantable multi-length antenna is in a different second medium;
- wherein the implantable multi-length antenna is configured to appear electrically as a first electrical length when in the first medium and as a different second electrical length when in the second medium, the implantable multi-length antenna including:
  - a first non-switchback segment;
  - a first switchback, electrically connected to the first non-switchback segment, the first switchback comprising first and second switchback segments; and
  - a second non-switchback segment electrically connected to the first switchback;
- wherein the second electrical length in the second medium is less than a physical length of the implantable multi-length antenna due at least in part to a capacitive coupling of the first switchback segment and the second switchback segment when in the second medium; and
- wherein the first operating frequency range is specified using the first electrical length and the second operating frequency range is specified using the second electrical length.

13. The method of claim 12, wherein the first operating frequency range is substantially equal to the second operating frequency range.

14. The method of claim 12, wherein the first operating frequency range includes at least one of:
- a medical implant communication service (MICS) range from approximately 402 MHz to 405 MHz;
- a short range device (SRD) range from approximately 862 MHz to 870 MHz;
- a first industrial scientific and medical (ISM) range from approximately 902 MHz to 928 MHz; or
- a second ISM range from approximately 2400 MHz to 2500 MHz.

15. The method of claim 12, wherein the first medium includes a dielectric material having a relative dielectric constant of approximately 1 and wherein the second medium includes a dielectric material having a relative dielectric constant greater than or equal to 5.0.

16. The method of claim 15, wherein the first medium is air and the second medium is a biological medium, wherein the biological medium includes at least one of bodily fluid, skin tissue, fat tissue, muscle tissue, organ tissue, or bone.

17. The method of claim 12, wherein the first electrical length of the implantable multi-length antenna when in the first medium is different than the second electrical length of the implantable multi-length antenna when in the second medium due at least in part to a difference in a relative dielectric constant of the first medium and a relative dielectric constant of the second medium.

18. The method of claim 12, wherein the first non-switchback segment is positioned approximately parallel to a first axis;
- wherein the first and second switchback segments comprising the first switchback are approximately parallel to a second axis, the second axis substantially perpendicular to the first axis;
- wherein the second non-switchback segment is approximately parallel to the first axis;
- wherein the implantable multi-length antenna includes a second switchback electrically connected to the second non-switchback segment, wherein the first switchback is positioned in a plane defined by the first axis and the second axis, wherein the second switchback is positioned in a plane defined by the first axis and a third axis, and wherein the third axis is substantially perpendicular to the first axis and different than the second axis.

19. The method of claim 12, wherein the implantable multi-length antenna includes:
- a second switchback electrically connected to the second non-switchback segment, the second switchback located a first distance from the first switchback;
- a third non-switchback segment electrically connected to the second switchback, the third non-switchback segment approximately parallel to the first axis; and
- a third switchback electrically connected to the third segment, the third non-switchback switchback located a different second distance from the second switchback.

20. The method of claim 19, comprising wirelessly transferring information electromagnetically at a specified third operating frequency range when the implantable multi-length antenna is in the first medium and at a specified fourth operating frequency range when the implantable multi-length antenna is in the second medium;
- wherein the third operating frequency range is different than the first operating frequency range and the fourth operating frequency range is different than the second operating frequency range;
- wherein the first operating frequency range and the second operating frequency range are specified using the first distance between the first switchback and the second switchback; and
- wherein the third operating frequency range and the fourth operating frequency range are specified using the second distance between the second switchback and the third switchback.

* * * * *